US007884075B2

(12) United States Patent
Scheiflinger et al.

(10) Patent No.: US 7,884,075 B2
(45) Date of Patent: *Feb. 8, 2011

(54) POLYMER-FACTOR VIII-VON WILLEBRAND FACTOR-CONJUGATES

(75) Inventors: Friedrich Scheiflinger, Vienna (AT); Peter Turecek, Klosterneuburg (AT); Juergen Siekmann, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 592 days.

This patent is subject to a terminal disclaimer.

(21) Appl. No.: 11/317,582

(22) Filed: Dec. 23, 2005

(65) Prior Publication Data

US 2006/0160948 A1 Jul. 20, 2006

(51) Int. Cl.
*A61K 38/37* (2006.01)
*C07K 14/775* (2006.01)

(52) U.S. Cl. .................. 514/14.1; 525/54.1; 530/383
(58) Field of Classification Search ............... None
See application file for complete search history.

(56) References Cited

U.S. PATENT DOCUMENTS

| | | | |
|---|---|---|---|
| 4,179,337 A * | 12/1979 | Davis et al. ........ | 435/181 |
| 4,356,170 A | 10/1982 | Jennings et al. | |
| 4,757,006 A | 7/1988 | Toole, Jr. et al. | |
| 4,877,608 A | 10/1989 | Lee et al. | |
| 4,965,199 A | 10/1990 | Capon et al. | |
| 4,970,300 A | 11/1990 | Fulton et al. | |
| 5,122,614 A * | 6/1992 | Zalipsky ............ | 548/520 |
| 5,298,643 A * | 3/1994 | Greenwald ......... | 558/6 |
| 5,328,694 A | 7/1994 | Schwinn | |
| 5,470,954 A | 11/1995 | Neslund et al. | |
| 5,539,063 A | 7/1996 | Hakimi et al. | |
| 5,565,427 A | 10/1996 | Freudenberg | |
| 5,605,884 A | 2/1997 | Lee et al. | |
| 5,618,788 A | 4/1997 | Capon et al. | |
| 5,621,039 A | 4/1997 | Hallahan et al. | |
| 5,733,873 A | 3/1998 | Osterberg et al. | |
| 5,763,401 A | 6/1998 | Nayar | |
| 5,846,951 A | 12/1998 | Gregoriadis | |
| 6,005,077 A | 12/1999 | Schwarz et al. | |
| 6,037,452 A * | 3/2000 | Minamino et al. .... | 530/383 |
| 6,379,933 B1 | 4/2002 | Jonson et al. | |
| 6,455,639 B1 | 9/2002 | Yasukohchi et al. | |
| 6,566,506 B2 | 5/2003 | Greenwald et al. | |
| 6,586,573 B1 | 7/2003 | Besman et al. | |
| 6,864,350 B2 | 3/2005 | Harris | |
| 7,199,223 B2 * | 4/2007 | Bossard et al. ...... | 530/383 |
| 2004/0132640 A1 | 7/2004 | DeFrees et al. | |
| 2004/0247624 A1 | 12/2004 | Unger et al. | |
| 2006/0160948 A1 | 7/2006 | Scheiflinger et al. | |

FOREIGN PATENT DOCUMENTS

| | | |
|---|---|---|
| EP | 0 774 261 A2 | 5/1997 |
| EP | 0 784 632 B1 | 1/1999 |
| EP | 0 977 584 B1 | 12/2001 |
| EP | 1 258 497 | 11/2002 |
| EP | 1 260 582 | 11/2002 |
| WO | 86/06096 A1 | 10/1986 |
| WO | WO 93/00357 | 1/1993 |
| WO | WO 94/15625 | 7/1994 |
| WO | WO 9415625 A1 * | 7/1994 |
| WO | WO 94/29370 | 12/1994 |
| WO | WO 97/11957 | 4/1997 |
| WO | WO 97/19701 | 6/1997 |
| WO | 98/25969 A1 | 6/1998 |
| WO | 98/38219 A1 | 9/1998 |
| WO | 00/49047 A1 | 8/2000 |
| WO | WO 01/05434 | 1/2001 |
| WO | WO 01/37893 | 5/2001 |
| WO | 03/040211 A2 | 5/2003 |
| WO | WO 2004/075923 | 9/2004 |
| WO | WO 2004/081053 | 9/2004 |
| WO | WO 2005/032581 | 4/2005 |
| WO | WO 2005/058366 | 6/2005 |

OTHER PUBLICATIONS

Avigad et al.; *J. Biol. Chem.*; 237; pp. 2736-2743 (1962).
Bi, et al.; *Nat. Genet.*; 10; pp. 119-121 (1995).
Brown et Bosak; *Thromb. Res.*; 43; pp. 303-311 (1986).
Denis, C., et al.; *Proceedings of the National Academy of Sciences USA*; vol. 95; pp. 9524-9529 (1998).
De Romeuf et Mazurier; *Thromb. Hamost.*; 69; pp. 436-440 (1993).
Elödi, et al.; *Thromb. Res.*; 21; pp. 695-700 (1981).
European Pharmacopoeia (Ph. Eur.) 3rd Ed.; 2.7.4 (1997).
Favaloro; *Thromb. Haemost.*; 83; pp. 127-135 (2000).
Fernandes et Gregoriadis; *Biochem. Biophys. Acta*; 1341; pp. 26-34 (1997).
Fischer, B.E., et al.; *Cellular and Molecular Life Science*; No. 53; pp. 943-950 (1997).
Fischer, B., et al.; *FEBS Letters 351*; pp. 345-348 (1994).
Fischer, B.E., et al.; *FEBS Letters 375*; pp. 259-262 (1995).
Girma et al.; *Thromb. Haemost.*; 74; pp. 156-160 (1995).
Jennings et Lugowski; *J. Immunol.*; 127; pp. 1011-1018 (1981).

(Continued)

*Primary Examiner*—Lisa J Hobbs
(74) *Attorney, Agent, or Firm*—Marshall, Gerstein & Borun LLP

(57) ABSTRACT

The present invention relates to a proteinaceous construct (also designated as polymer-VWF-conjugate) comprising plasmatic and/or recombinant von Willebrand factor (VWF), said VWF being bound to at least one physiologically acceptable polymer molecule, as well as to a complex between said proteinaceous construct and at least one factor VIII (FVIII) protein. The physiologically acceptable polymer molecule can be, for instance, polyethylene glycol (PEG) or polysialic acid (PSA). Further the present invention relates to methods for prolonging the in vivo-half-life of VWF or FVIII in the blood of a mammal having a bleeding disorder associated with functional defects of or deficiencies of at least one of FVIII or VWF.

85 Claims, 27 Drawing Sheets

OTHER PUBLICATIONS

Kaersgaard et Barington; *J. Chromatogr.*; B715; pp. 357-367 (1998).
Lankhof et al.; *Thromb. Haemost.*; 77; pp. 1008-1013 (1997).
Lee et al.; *Pharm. Res.*; 20; pp. 818-825 (2003).
Lenting, P.J., et al.; *The Journal of Biological Chemistry*; vol. 279:13; pp. 12102-12109 (2004).
Macfarlane et al.; *Thromb. Diath. Haemorrh.*; 34; pp. 306-308 (1975).
Migneault et al.; *Biotechniques*; 37; pp. 790-796 (2004).
Pietu et al.; *Biochem. Biophys. Res. Commun.*; 164; pp. 1339-1347 (1989).
Roberts et al.; *Advanced Drug Delivery Reviews*; 54; pp. 459-476 (2002).
Roussi, J., et al.; *Blood Coagulation and Fibrinolysis*; vol. 9:4; pp. 361-372 (1998).
Ruggeri et al.; *Blood*; vol. 57; No. 6; pp. 1140-1143 (1981).
Ruggeri et al.; *Thromb. Haemost.*; 82; pp. 576-584 (1999).
Schlokat, U., et al.; *Biotechnology and Applied Biochemistry*; vol. 24; pp. 257-267 (1996).
Schwarz, H.P., et al.; *Haemophilia*; vol. 4:3; pp. 53-62 (1998).
Schwarz, H.P., et al.; *Seminars in Thrombosis and Hemostasis*; vol. 28:2; pp. 215-225 (2002).
Turecek et al.; *Semin. Thromb. Hemost.*; 28 ; pp. 149-160 (2002).
Turecek, P.L., et al.; *Blood*; vol. 90:9; pp. 3555-3567 (1997).
Weiss, H.J., et al.; *The Journal of Clinical Investigation*; vol. 52; pp. 2708-2716 (1973).
Wilchek et. Bayer; *Meth. Enzylmol.*; 138; pp. 429-442 (1987).
Office Action in U.S. Appl. No. 12/184,567, mailed Dec. 29, 2008.
Blood coagulation factor derivatives with side chain of amino acids moiety bound via coupling agent to poly:alkylene glycol [abstract], Derwent, Sep. 29, 1984, (JP 01 742043, Nippon Chemiphar Co., Mar. 15, 1993).
Gregoriadis et al., Polysialic acids: potential in drug delivery, FEBS Lett., 315:271-276, 1993.
Gregoriadis et al., Polysialic acids: potential in improving the stability and pharmokinetics of proteins and other therapeutics, CMLS Cell. Mol. Life Sci., 57:1964-1969, 2000.
Gregoriadis et al., Polysialylated proteins: an approach to improving enzyme stability and half-life in the blood circulation, Sciences Techniques et Pratiques STP, 9:61-66, 1999.
International Search Report, PCT/US2005/046879, European Patent Office, mailed Jun. 19, 2007.
Jain et al., Polysialylated insulin: synthesis, characterization and biological activity in vivo, Biochim. Biophys. Acta, 1622:42-49, 2003.
Jain et al., Polysialylation: the natural was to improve the stability and pharmacokinetics of protein and peptide drugs, DDS&S, 4:3-9, 2004.
Lewis et al., A facile, water-soluble method for modification of proteins with DOTA: use of elevated temperature and optimized pH to achieve high specific activity and high chelate stability in radiolabeled immunoconjugates, Bioconj. Chem., 6:565-576, 1994.
Luo et al., A hyaluronic acid-taxol antitumor bioconjugate targeted to cancer cells [abstract], Biomacromolecules, 1:208-218, 2000.
Luo et al., Synthesis and selective cytotoxicity of a hyaluronic acid-antitumorbioconjugate [abstract], Bioconj. Chem., 10:755-763, 1999.
Saenko et al., Strategies towards a longer acting factor VIII, Haemophilia, 12:42-51, 2006.
Turecek et al., Modification of rVWF with polysialic acid: biochemical and functional characterization in mice with VWD, Blood, 108:298A-299A, 2006.
Turecek et al., PDG modified rVFW prolongs the survival of native rFVIII in hemophilia A knock-out mice, Blood, 108:299A, 2006.
Written Opinion of the International Searching Authority, PCT/US2005/046879, European Patent Office, mailed Jun. 19, 2007.

\* cited by examiner

POLYMER-FACTOR VIII-VON WILLEBRAND FACTOR-CONJUGATES

FIELD OF THE INVENTION

The present invention relates to a proteinaceous construct comprising plasmatic and/or recombinant von Willebrand factor (VWF), said VWF being bound to at least one physiologically acceptable polymer molecule, as well as to a complex between said proteinaceous construct and at least one factor VIII (FVIII) protein. Further the present invention relates to methods for prolonging the in vivo half-life of VWF or FVIII in the blood of a mammal having a bleeding disorder associated with functional defects or deficiencies of at least one of FVIII or VWF.

BACKGROUND OF THE INVENTION

VWF is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The precursor polypeptide, pre-pro-VWF, consists of a 22-residue signal peptide, a 741-residue pro-peptide and the 2050-residue polypeptide found in mature plasma VWF (Fischer et al., FEBS Lett. 351: 345-348, 1994). Upon secretion into plasma VWF circulates in the form of various species with different molecular sizes. These VWF molecules consist of oligo- and multimers of the mature subunit of 2050 amino acid residues. VWF can be usually found in plasma as one dimer up to multimers consisting of 50-100 dimers (Ruggeri et al. Thromb. Haemost. 82: 576-584, 1999). The in vivo half-life of human VWF in the human circulation is approximately 12 to 20 hours.

The most frequent inherited bleeding disorder in humans is von Willebrand's disease (VWD), which can be treated by replacement therapy with VWF containing concentrates of plasmatic or recombinant origin. Due to the short half-life of VWF in blood there is a strong need to develop VWF concentrates with a prolonged in vivo half-life of VWF. The same applies to FVIII, which has also a relatively short in vivo half-life of approximately 8 to 12 hours requiring frequent re-dosing for patient treatment of bleeding disorders associated with functional defects of or deficiencies of at least one of FVIII and VWF.

In the prior art it has been described that recombinant VWF (rVWF) produced in an eucaryotic cell culture is more intact and less proteolytically degraded than plasma-derived VWF (Fischer et al., FEBS Lett. 375: 259-262, 1995). EP 0 784 632 describes a method for isolating highly pure VWF by purifying recombinant VWF using anion exchange chromatography. Methods for a large scale production of homogenous and structurally intact VWF are also known in the art (Schlokat et al., Biotechnol. Appl. Biochem. 24: 257-267, 1996; Fischer et al., CMLS 53: 943-950, 1997). Recombinant VWF has been characterized by using canine, murine, and porcine models of von Willebrand's disease (VWD) (Turecek et al., Blood 90: 3555-3567, 1997; Roussi et al., Blood Coag. Fibrinol. 9: 361-372, 1998; Schwarz et al., Haemophilia 4: 53-62, 1998; Schwarz et al., Semin. Thromb. Hemost. 28: 215-225, 2002). WO 00/49047 describes a method for producing a VWF preparation by treating pro-VWF with thrombin. A method for purifying proteins that bind to VWF by using a rVWF immobilized on a carrier is disclosed in WO 98/25969. The pharmaceutical use of plasma derived and recombinant VWF pro-peptides (pro-VWF) for treating blood coagulation disorders is described in EP 0 977 584. U.S. Pat. No. 6,037,452 describes the binding of FVIII and factor IX (FIX) to a poly (alkylene oxide) through a linker or a coupling agent. In EP 0 774 261 it is shown that the use of recombinant VWF having a prolonged biological in vivo half-life stabilizes FVIII in the blood of a mammal and induces the production of endogenous FVIII. Nevertheless, there exists a need for patients having VWF- or FVIII-based bleeding disorders to further increase the in vivo half-life of VWF and FVIII.

VWF is known to stabilize FVIII in vivo and, thus, plays a crucial role to regulate plasma levels of FVIII and as a consequence is a central factor to control primary and secondary hemostasis. It is also known that after application of therapeutic products containing VWF an increase in endogenous FVIII:C to 1 to 3 units per ml in 24 hours can be observed demonstrating the in vivo stabilizing effect of VWF on FVIII.

A strong need exists for a new substance for widening the treatment spectrum for deficiencies in coagulation FVIII also known as hemophilia A and/or qualitative or quantitative deficiencies of VWF also known as VWD. Due to a lack of functional VWF, patients with VWD have a secondary defect of FVIII represented by FVIII plasma levels below normal. Depending on the type of VWD and the severity of the diseases these FVIII levels can vary but are generally measurably lower than the FVIII plasma level found in healthy humans.

Thus, the present invention provides a novel system for prolonging the in vivo half-life of VWF and/or of FVIII in the blood of a mammal. It is a further object of the present invention to provide methods for the improved treatment of bleeding disorders associated with functional defects of or deficiencies of one or both of FVIII and VWF.

SUMMARY OF THE INVENTION

The present invention relates to a proteinaceous construct comprising plasmatic and/or recombinant von Willebrand factor (VWF) or biologically active derivatives thereof, said VWF or said biologically active derivatives thereof being bound to one or more physiologically acceptable polymer molecules, wherein the in vivo half-life of the proteinaceous construct is prolonged in the blood of a mammal, particularly a human. Further, the present invention relates to a complex between said proteinaceous construct and at least one factor FVIII (FVIII) protein or a biologically active derivative thereof, wherein the in vivo half-life of said FVIII protein or said biologically active derivative thereof is also prolonged in the blood of a mammal. Additionally, pharmaceutical compositions containing said proteinaceous construct or said complex as well as methods for prolonging the in vivo half-life of VWF or FVIII in the blood of a mammal having a bleeding disorder associated with functional defects of or deficiencies of at least one of FVIII and VWF using said proteinaceous construct or said complex are provided according to the present invention. Methods for making the proteinaceous construct are also provided.

DETAILED DESCRIPTION OF THE INVENTION

One aspect of the present invention relates to a proteinaceous construct (in the following also designated as "polymer-VWF-conjugate") comprising plasmatic and/or recombinant VWF or biologically active derivatives thereof, said VWF or said biologically active derivatives thereof being bound to one or more types of physiologically acceptable polymer molecules, wherein the in vivo half-life of said VWF or said biologically active derivatives thereof is prolonged in the blood of a mammal.

It is a further aspect of the present invention to provide polymer-VWF-conjugates, which follow two principal pharmacological mechanisms and of forms of said polymer-VWF-conjugates having features in-between said two forms. One form stably carries the polymer conjugated to VWF and will be eliminated as an integral molecule over time after application to a mammal. The other form is characterized by reversibility of the polymer conjugated to VWF. After administration to a mammal, the polymer molecules bound to VWF will be gradually released from VWF and non-conjugated VWF will become available as the pharmacologically functional agent. The release characteristics will depend on the conjugation chemistry and on the composition and the structure of the polymer molecules bound to VWF.

The polymer-VWF conjugates are useful either alone for treatment of VWD, or combined with FVIII to stabilize FVIII for increased half-life or both. When used solely for the treatment of VWD, the conjugate may take one of two forms. The first form is where the polymer is releasably bound to the VWF. In this manner the VWF becomes active as the polymer is released or degrades. The second form is where the polymer concentration bound to the VWF is such so as to not interfere with the VWF activity. When the conjugate is prepared to bind with and stabilize FVIII, the degree or level of polymer bound to the VWF is provided so as to not interfere with the binding region of the VWF. As will be shown in the examples, satisfactory polymer conjugation to the VWF can be achieved without interfering with the VWF and FVIII binding capacity. The degree of polymer conjugation can also be controlled or modified to maintain VWF activity while also maintaining the ability of the VWF to bind FVIII. In this form the polymer-VWF conjugates provide a therapeutically active VWF, while also stabilizing FVIII for increased half-life.

The VWF and FVIII molecules useful for the present invention include the full length protein, precursors of the protein, subunits or fragments of the protein, and functional derivatives thereof. Reference to VWF and FVIII or FVIII is meant to include all potential forms of such proteins.

As used herein "biologically active derivative" includes any derivative of a molecule having substantially the same functional and/or biological properties of said molecule, such as binding properties, and/or the same structural basis, such as a peptidic backbone or a basic polymeric unit.

The VWF useful for the present invention includes all potential forms, including the monomeric and multimeric forms. One particularly useful form of VWF are homo-multimers of at least two VWFs. The VWF proteins may be either a biologically active derivative, or when to be used solely as a stabilizer for FVIII the VWF may be of a form not biologically active. It should also be understood that the present invention encompasses different forms of VWF to be used in combination. For example, a composition useful for the present invention may include different multimers, different derivatives and both biologically active derivatives and derivatives not biologically active. In primary hemostasis VWF serves as a bridge between platelets and specific components of the extracellular matrix, such as collagen. The biological activity of VWF in this process can be measured by two different in vitro assays (Turecek et al., Semin. Thromb. Hemost. 28: 149-160, 2002). The ristocetin cofactor assay is based on the agglutination of fresh or formalin-fixed platelets induced by the antibiotic ristocetin in the presence of VWF. The degree of platelet agglutination depends on the VWF concentration and can be measured by the turbidimetric method, e.g. by use of an aggregometer (Weiss et al., J. Clin. Invest. 52: 2708-2716, 1973; Macfarlane et al., Thromb. Diath. Haemorrh. 34: 306-308, 1975). The second method is the collagen binding assay, which is based on ELISA technology (Brown et Bosak, Thromb. Res. 43: 303-311, 1986; Favaloro, Thromb. Haemost. 83: 127-135, 2000). A microtiter plate is coated with type I or III collagen. Then the VWF is bound to the collagen surface and subsequently detected with an enzyme-labeled polyclonal antibody. The last step is the substrate reaction, which can be photometrically monitored with an ELISA reader.

As used herein, "plasma-derived VWF (pdVWF)" includes all forms of the protein found in blood including the mature VWF obtained from a mammal having the property of in vivo-stabilizing, e.g. binding, of at least one FVIII molecule. However, the invention is not limited to the mature VWF. One, biologically active derivative of said pVWF is pro-VWF which contains the pro-peptide. Other forms of VWF useful for the present invention include the proteinaceous construct comprises immature VWF including the precursor VWF molecule (pre-pro-VWF) synthesized by endothelial cells and megakaryocytes, and/or the VWF propeptide (pro-VWF) and/or mature pdVWF obtained upon cleavage of the signal peptide and pro-peptide, respectively of the precursor molecule. Further examples of biologically active derivatives of pdVWF include pro-drugs which are processed or converted into the biologically active form, or is biologically active as such, truncated forms, forms having deletions, forms having substitutions, forms having additions other than pro-forms, fragments of the mature form, chimeric forms, and forms having post-translational modifications as compared to the natural form. PdVWF useful for the present invention also includes those forms not biologically active. This may be accomplished by modification of the mature VWF or other naturally occurring forms found in blood. The source for VWF useful for the invention is mammalian, including porcine and human versions.

As used herein, "recombinant VWF (rVWF)" includes VWF obtained via recombinant DNA technology. One form of useful rVWF has at least the property of in vivo-stabilizing, e.g. binding, of at least one FVIII molecule and having optionally a glycosylation pattern which is pharmacologically acceptable. Specific examples thereof include VWF without A2 domain thus resistant to proteolysis (Lankhof et al., Thromb. Haemost. 77: 1008-1013, 1997), the VWF fragment from Val 449 to Asn 730 including the glycoprotein lb-binding domain and binding sites for collagen and heparin (Pietu et al., Biochem. Biophys. Res. Commun. 164: 1339-1347, 1989). The determination of stabilizing at least one FVIII molecule can be carried out in VWF-deficient mammals according to methods known in the state in the art. For example, as described in Example 8 below, VWF-deficient mice are treated intravenously via the tail vein with VWF, and the level of FVIII activity in their plasma is followed over time. The level of FVIII activity can be measured by, for instance, a chromogenic assay such as published in the European Pharmacopoeia (Ph. Eur., $3^{rd}$ Ed. 1997:2.7.4).

The sample, containing FVIII (FVIII:C) is mixed with thrombin, activated factor IX (FIXa), phospholipids and factor X (FX) in a buffer containing calcium. FVIII is activated by thrombin and subsequently forms a complex with phospholipids, FIXa and calcium ions. This complex activates FX to FXa, which in turn cleaves a chromogenic substrate (e.g. (AcOH*$CH_3$OCO-D-CHA-Gly-Arg-pNA). The time course of para-nitroaniline (pNA) released is measured at 405 nm. The slope of the reaction is proportional to the FVIII concentration in the sample.

The rVWF of the present invention may be produced by any method known in the art. One specific example is disclosed in WO86/06096 published on Oct. 23, 1986 and U.S. patent application Ser. No. 07/559,509, filed on Jul. 23, 1990, in the name of Ginsburg et al., which is incorporated herein by reference with respect to the methods of producing recombinant VWF. This may include any method known in the art for (i) the production of recombinant DNA by genetic engineering, e.g. via reverse transcription of RNA and/or amplification of DNA, (ii) introducing recombinant DNA into procaryotic or eucaryotic cells by transfection, e.g. via electroporation or microinjection, (iii) cultivating said transformed cells, e.g. in a continuous or batchwise manner, (iv) expressing VWF, e.g. constitutively or upon induction, and (v) isolating said VWF, e.g. from the culture medium or by harvesting the transformed cells, in order to (vi) obtain purified rVWF, e.g. via anion exchange chromatography or affinity chromatography.

The rVWF can be produced by expression in a suitable prokaryotic or eukaryotic host system characterized by producing a pharmacologically acceptable VWF molecule. Examples of eukaryotic cells are mammalian cells, such as CHO, COS, HEK 293, BHK, SK-Hep, and HepG2. There is no particular limitation to the reagents or conditions used for producing or isolating VWF according to the present invention and any system known in the art or commercially available can be employed. In a preferred embodiment of the present invention rVWF is obtained by methods as described in the state of the art.

A wide variety of vectors can be used for the preparation of the rVWF and can be selected from eukaryotic and prokaryotic expression vectors. Examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAc5, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived from viral systems such as vaccinia virus, adeno-associated viruses, herpes viruses, retroviruses, etc., using promoters such as CMV, SV40, EF-1, UbC, RSV, ADV, BPV, and β-actin.

The FVIII useful with the present invention includes those forms, which are biologically active including the full length FVIII and any derivative capability of acting as a cofactor in the activation of coagulation FIX and the capability of forming a complex with VWF. The FVIII used according to the present invention may be a plasma-derived FVIII (pdFVIII) or a recombinant FVIII (rFVIII) or biologically active derivatives thereof. The pdFVIII and the rFVIII may be produced by any method known in the art. PdFVIII may be purified by any suitable means. One useful method is described in U.S. Pat. No. 5,470,954, which is incorporated herein by reference. RFVIII proteins may be prepared by any suitable means. Examples of such rFVIII include RECOMBINATE and ADVATE both manufactured and sold by Baxter Healthcare Corporation; REFACTO, a B-domain deleted form of FVIII manufactured and sold by Wyeth Corporation; and KOGENATE, manufactured and sold by Bayer Corporation. Methods and examples of rFVIII are described in U.S. Pat. Nos. 4,757,006; 4,965,199; and 5,618,788, all of which are incorporated herein by reference.

As used herein, "physiologically acceptable polymer" includes polymers which are soluble in an aqueous solution or suspension and have no negative impact, such as side effects, to mammals upon administration of the polymer-VWF-conjugate in a pharmaceutically effective amount. There is no particular limitation to the physiologically acceptable polymer used according to the present invention. The polymers are typically characterized as having preferably from 2 to about 300 repeating units. Examples of such polymers include, but are not limited to, poly(alkylene glycols) such as polyethylene glycol (PEG), poly (propylene glycol) (PPG), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), and combinations of any of the foregoing.

The physiologically acceptable polymer is not limited to a particular structure and can be linear (e.g. alkoxy PEG or bifunctional PEG), branched or multi-armed (e.g. forked PEG or PEG attached to a polyol core), dendritic, or with degradable linkages. Moreover, the internal structure of the polymer can be organized in any number of different patterns and can be selected from the group consisting of homopolymer, alternating copolymer, random copolymer, block copolymer, alternating tripolymer, random tripolymer, and block tripolymer.

These polymers also include poly(alkylene oxide) polymers, poly(maleic acid), poly(DL-alanine), such as carboxymethylcellulose, dextran, hyaluronic acid and chitin, and poly(meth)acrylates.

In an embodiment of the present invention, the physiologically acceptable polymer is PEG and derivatives thereof. The PEG side chain can be linear, branched, forked or can consist of multiple arms. There is no specific limitation of the PEG used according to the present invention. A particularly useful PEG has a molecular weight in the range of 3,000-20,000. There are several useful PEG molecules that are in the public domain, i.e. that were never patented or are now off-patent. Other useful PEG molecules are disclosed in WO 03/040211; U.S. Pat. No. 6,566,506; U.S. Pat. No. 6,864,350; and U.S. Pat. No. 6,455,639, for example.

In another embodiment of the present invention, the physiologically acceptable polymer is polysialic acid (PSA) and derivatives thereof. PSA can be bound to VWF by the method described in U.S. Pat. No. 4,356,170, which is herein incorporated by reference. In one embodiment of the invention the polysaccharide compound may be naturally occurring polysaccharide, a derivative of a naturally occurring polysaccharide, or a naturally occurring polysaccharide derivative. The polysaccharide portion of the compound has more than 5, typically at least 10, and in another embodiment at least 20 to 50 sialic acid residues in the polymer chain. Readily available polysaccharide compounds may have up to 500 saccharide residues in total, but usually have fewer than 300 residues in the polymer chain. Generally, all of the saccharide residues in the compound are sialic acid residues.

The polysialic acid portion at least of the polysaccharide compound, and in one embodiment the entire compound, is highly hydrophilic. Hydrophilicity is conferred primarily by the pendant carboxyl groups of the sialic acid units, as well as the hydroxyl groups. The saccharide unit may contain other functional groups, such as, amine, hydroxyl or sulphate groups, or combinations thereof. These groups may be present on naturally occurring saccharide compounds, or introduced into derivative polysaccharide compounds.

Polysaccharide compounds of particular use for the invention are those produced by bacteria. Some of these naturally occurring polysaccharides are known as glycolipids. It is particularly advantageous if the polysaccharide compounds are substantially free of terminal galactose units, which tend to be recognized by galactose receptors of hepatocytes and Kupffer cells.

The VWF multimers may be covalently linked to the polysaccharide compounds by any of various techniques known to those of skill in the art. Examples include linkage through the peptide bond between a carboxyl group on one of either the vWF or polysaccharide and an amine group of the other, or an ester linkage between a carboxyl group of one and a hydroxyl group of the other. Alternatively a Schiff base can be formed between an amino group of one and an aldehyde group of the other. Other mechanisms of linkage are within the ordinary skill of the art. Various examples are identified at column 7, line 15, through column 8, line 5 of U.S. Pat. No. 5,846,951, all of which are incorporated by reference.

As used herein, reference to the VWF being bound to one or more physiologically acceptable polymer molecules includes any suitable chemical binding, such as, covalently bound or non-covalently bound such as ionic, hydrophobic, affinity, bioaffinity interactions. The polymer can also be coupled to the protein by use of bifunctional reagents and via a spacer arm. In addition the polymer molecule can be coupled to the VWF by affinity interaction. For example, the VWF can be biotinylated and avidin or strepavidin conjugated polymers can be bound to the VWF. In addition polyclonal or monoclonal anti-VWF antibodies as well as fragments thereof can be bound to a polymer and then this complex can be bound to the VWF. Polymers can be bound to the VWF also by enzymatical methods such as, for example, the transfer of saccharides with polyglycosyltransferase as taught in U.S. Pat. No. 6,379,933 or glycopegylation as taught in US 2004 0132640 A1, all of which teachings are incorporated herein by reference. Another approach is the binding of polymers to the VWF on the basis of their biological function like the binding of PEGylated collagens or collagen fragments to the A1 and A3 domains of the VWF. For this purpose collagens from type I and III, e.g. from human placenta, showing a strong interaction with the VWF can be used. The binding of the polymers may be stable or reversible after in vivo application of the proteinaceous construct.

As used herein, "PEGylated VWF" includes VWF which is bound to one or more PEGs, and as used herein "PEGylation" includes the process of binding one or more PEGs to VWF. Suitable methods of PEGylation are disclosed in U.S. Pat. Nos. 5,122,614 and 5,539,063, all of which PEGylation methods are incorporated by reference.

According to an embodiment of the present invention the physiologically acceptable polymer is PEG or a PEG derivative, which is covalently linked to VWF by any strategy and method known in the art. The most common modification strategies are the binding of at least one polymer molecule via amino groups of lysine residues, the binding of at least one polymer molecule via carbohydrate side chains, the binding of at least one polymer molecule via sulfhydryl groups, the binding of at least one polymer molecule via carboxyl groups of aspartic acids and glutamic acids as well as the binding of at least one polymer molecule of hydroxyl groups and the binding of at least one polymer molecule of the N-terminus.

In one embodiment of the present invention the binding of at least one polymer molecule to VWF can be performed by covalently coupling said polymer molecule to the amino groups of the lysine side chains of VWF. Human VWF contains free 108 lysine residues with $NH_2$ groups in the side chains, which are susceptible to binding of at least one polymer molecule. Examples of lysine residues of VWF to which the polymer molecule may be covalently linked according to the present invention are shown in FIG. 1A. Suitable PEG derivatives which may be covalently linked to the lysine residues of VWF are, for example, polyethylene glycols with an active N-hydroxysuccinimide ester (NHS) such as succinimidyl succinate, succinimidyl glutarate or succinimidyl propionate, which react with the lysine residues under mild conditions by forming an amide bond. Other examples of activated PEG are those with an active carbonate such as succinimidyl carbonate (SC-PEG) and benzotriazole carbonate (BTC-PEG) (see page 463 of Roberts et al., Advanced Drug Delivery Reviews 54: 459-476, 2002). SC-PEG and BTC-PEG react preferentially with lysine residues to form a carbamate linkage, but are also known to react with histidine and tyrosine residues. Alternative methods are the binding of at least one polymer molecule with PEG carbonates forming urethane bonds or with aldehydes or ketones forming secondary amines, e.g. after reduction with sodium cyano borohydride. Other PEG acylating reagents which produce urethane linked proteins include p-nitrophenyl carbonate, trichlorophenyl carbonate, and carbonylimidazole. These reagents are prepared by reacting chloroformates or carbonylimidazole with the terminal hydroxyl group on monomethoxyPEG (mPEG) (see p. 464 of Roberts et al., above). Another example relates to so-called "second generation" PEGylation chemistry whereby mPEG-propionaldehyde, under acidic conditions, is selective for the N-terminal a-amine (see page 464 of Roberts et al., above). Releasable PEG reagents such as PEG maleic anhydride, mPEG phenyl ether succinimidyl carbonates, and mPEG benzamide succinimidyl carbonates, may be used to produce a conjugate which, under physiological conditions, will release the therapeutic protein with "no tag", as described on page 469 of Roberts et al., above.

In a further embodiment of the present invention, VWF can be also bound to at least one polymer molecule via its carbohydrate residues. This can be carried out by e.g. mild oxidation of the carbohydrate chains, such as with $NaIO_4$, forming an aldehyde function and subsequent coupling to a PEG, such as PEG-hydrazide. An advantage of this procedure is based on the fact that the A1 and A3 loops of VWF, which comprise the collagen binding sites and therefore are critical regions for the biological activity of VWF, contain no carbohydrate residues and might not be modified by this procedure as can be seen in FIG. 1B. This figure shows an example of the asparagine N-linked linked GlcNAc and the threonine- or serine O-linked GalNAc residues, which can be oxidized and subsequently bound by at least one polymer molecule. Due to the fact that the carbohydrates of the VWF are clustered in certain domains, the VWF might be site directed bound by at least one polymer molecule by use of this modification procedure. The binding of polymer to the carbohydrate residue is particularly advantageous when the therapeutically active form of the VWF is desired. This can be enhanced by selective reaction of the polymer to either the N-linked or O-linked residues through known methods. For instance, the enzyme glucose oxidase can be used to oxidate carbohydrate residues on VWF to generate multiple reactive aldehyde groups, which can be reacted with PEG-hydrazide to produce a hydrazone linkage or with PEG-amine to produce a reversible Schiff base (see page 467 of Roberts et al., above). Under certain conditions, an N-terminal serine or threonine of VWF can be used for site-specific conjugation by converting it to a glyoxylyl derivative by periodate oxidation (see page 467 of Roberts et al., above).

Another embodiment of the present invention is the binding of at least one polymer molecule to VWF via sulfhydryl groups. Human VWF has 177 free SH-groups, which can be modified, for example, by PEG maleimide forming a stable sulfide. PEGylation of cysteine residues may also be carried out using, for instance, PEG-vinylsulfone, PEG-iodoacetamide, or PEG-orthopyridyl disulfide (see page 466 of Roberts et al., above).

According to its multiple functions the VWF molecule has several binding sites to specific receptors or ligands (Girma et al., Thromb Haemost. 74:156-60, 1995). One important binding site is the FVIII binding domain, which is located at the N-terminus of the mature subunit (amino acids 1-272). This epitope can be protected by incubation with free FVIII and formation of a FVIII/VWF complex. Subsequently the complex is chemically modified (e.g. PEGylated or polysialylated) and the polymer-conjugated VWF with free FVIII binding site is separated from the FVIII (e.g. by size exclusion chromatography with 0.3 M $CaCl_2$ or 2M NaCl). Similarly the VWF can be bound to an affinity resin with immobilized FVIII. Subsequently the VWF is chemically conjugated with a polymer (e.g. a polyethylene glycol or polysialic acid derivative) and eluted from this matrix (e.g. under high salt conditions such as 0.3 M $CaCl_2$ or 2 M NaCl) in a batch mode or by use of a chromatography column.

The FVIII binding epitope of VWF is nearly identical with the heparin-binding site. Thus, the FVIII binding site can be blocked and protected by binding of VWF to heparin or to an affinity resin with immobilized heparin during the chemical modification procedure.

As used herein, the term "Factor VII-binding-site-protecting agent" refers to any agent which binds to the FVIII binding domain or epitope on the VWF molecule. A Factor VIII-binding-site-protecting agent may be selected from Factor VII, derivatives of FVIII, heparin, and derivatives of heparin.

The present invention is directed to increasing in vivo half-life of VWF or biologically active derivatives thereof as compared to the in vivo half-life of VWF not linked to at least one physiologically acceptable polymer molecule. In one embodiment of the present invention, the in vivo half-life of VWF is prolonged for at least a factor of two, while in another embodiment the in vivo half-life is increased for at least a factor of three. In still another embodiment the in vivo half-life is increased by a factor of five by binding of at least one physiologically acceptable polymer molecule. The increase or prolonging of VWF half-life can be assessed by measuring the pharmacokinetics of VWF in FVIII deficient mice, as described in Example 7 below. Briefly, FVIII deficient mice are treated with a bolus injection of VWF premixed with FVIII via the tail vein, and VWF antigen levels are measured in plasma samples at various time points. VWF antigen, as well as FVIII antigen, can be measured via ELISA assay.

A further aspect of the present invention relates to a complex formed between at least one polymer-VWF-conjugate and at least one FVIII molecule, wherein the in vivo half-life of the FVIII is prolonged in the blood of a mammal by the polymer-VWF-conjugate.

The binding of the polymer-VWF-conjugate with FVIII prolongs or increases the in vivo half-life of said FVIII as compared to the in vivo half-life of a FVIII forming a complex with VWF not linked to at least one physiologically acceptable polymer molecule. In an embodiment of the present invention, the in vivo half-life of FVIII is prolonged for at least a factor of 1.5, in another embodiment for at least a factor of two, in another embodiment for at least a factor of three, and in a further embodiment for at least a factor of five.

The polymer-VWF-conjugates of the present invention can be used for the treatment of hemophilia A and/or VWD or subtypes of these two diseases. In the case of VWD, the use of polymer-VWF-conjugates will be similar to current substitution therapy with VWF containing concentrates by either regular or irregular treatment, also referred to as prophylaxis protocols or on demand treatment respectively. Polymer-VWF-conjugates can also be used as an adjuvant treatment of hemophilia A prophylaxis. Under these treatment circumstances polymer-VWF-conjugates will be administered in time intervals and independently FVIII concentrates, either plasma-derived or recombinant, the same which are currently used for regular treatment of hemophilia A, will be given as usual, however, with prolonged treatment intervals due to the half-life prolonging capabilities of polymer-VWF-conjugates.

In one embodiment of the invention for both the prophylaxis in hemophilia A and VWD and for treatment of acute bleeds in hemophilia A and VWD, a polymer-VWF-conjugate will be administered together with FVIII or in the form of a complex with FVIII to patients with hemophilia A or VWD. In such cases arrest of internal or external bleedings needs to be achieved immediately by raising the otherwise low plasma levels of either VWF and/or FVIII to therapeutically effective levels. The polymer-VWF-conjugates can also be used for immunotolerance therapy to eradicate inhibitory antibodies, which have developed against FVIII, a clinical situation also known as inhibitor hemophilia, or against VWF. Under such circumstances supra-physiological and supra-pharmacological levels of FVIII are administered to patients having developed inhibitors against either FVIII or VWF. This form of therapy is facilitated by application of polymer-VWF-conjugates having usually higher recoveries and longer persistence in the circulation of patients receiving said preparations than non-conjugated VWF.

According to the state of the art in therapy and according to international guidelines and regulations, the pharmacokinetics of infused FVIII are recognized and accepted as valid surrogate markers for efficacy. This is based on the validated assumption that an infused FVIII product which had been characterized by standardized tests for functional activity will be found in the blood stream and will act there as expected as a cofactor of the tenase-complex, the activation complex of factor X by binding to FIXa and phospholipids. (Elödi et al., Thromb. Res. 21: 695-700, 1981). Therefore any pharmacokinetic analysis in animal models will be predictive for efficacy expected in patients treated with FVIII products.

For the determination of FIX cofactor activity a FVIII or FVIIIa sample (FVIII completely activated with thrombin) is added to a prepared mixture of FIXa, FX, phospholipid and $CaCl_2$. This reaction mix is incubated at 37° C. to allow complex formation and subsequent FXa generation. Sub-samples are drawn at intervals up to 20 minutes and added to a chromogenic substrate, which is selectively split by FXa. After 15 minutes of incubation, the reaction is terminated by the addition of acetic acid. The absorbance ($A_{405}$) values, which are proportional to the FXa concentrations, are measured in an ELISA reader and plotted against the incubation time in the reaction mix.

A further aspect of the present invention is the provision of a method for prolonging the in vivo half-life of FVIII in the blood of a mammal having a bleeding disorder associated with functional defects of or deficiencies of at least one of FVIII and VWF, comprising the steps of:
 a) providing at least one proteinaceous construct as defined above;
 b) providing at least one FVIII as defined above; and
 c) forming a complex between said proteinaceous construct and said FVIII.

In one embodiment of the above method the complex of step (c) is formed "extracorporeal" (i.e. outside of the body of a mammal) by e.g. mixing the proteinaceous construct and said FVIII, and then administering the thus formed complex in an effective amount to the mammal having said bleeding disorder.

In a further embodiment of the above method, the complex of step (c) is formed intracorporeal (i.e. inside of the body of a mammal) between the proteinaceous construct and endogenous FVIII present in the blood of a mammal having said bleeding disorder upon administering the proteinaceous construct in an effective amount to said mammal.

In yet another embodiment of the above method the complex of step (c) is formed "intracorporeal" between the proteinaceous construct and exogenous FVIII present in the blood of a mammal having said bleeding disorder upon administering the proteinaceous construct in an effective amount to said mammal. Exogenous FVIII may be administered simultaneously in an effective amount with said proteinaceous construct or sequentially, i.e. before or after administering said proteinaceous construct.

As used herein, "endogenous FVIII" includes FVIII which originates from said mammal. It also includes FVIII transcribed from a transgene or any other foreign DNA present in said mammal. As used herein, "exogenous FVIII" includes FVIII which does not originate from said mammal including pdFVIII and rFVIII as outlined above, as well as pdFVIII which is re-administered to the mammal from which it was isolated after forming the above-defined complex, and rFVIII which is administered to the mammal whose DNA has been used in the production of said rFVIII.

As used herein, "effective amount" includes a dose suitable for treating a mammal having a bleeding disorder as outlined above; for example, for humans preferably in a range from 5 to 1,000 IU per infusion and more preferably in a range from 10 to 250 IU per infusion.

The route of administration does not exhibit particular limitations, and in one embodiment the proteinaceous construct or the complex of the present invention may be administered by injection, such as intravenous, intramuscular, or intraperitoneal injection.

The present invention is also directed at treating bleeding disorders associated with functional defects of or deficiencies of at least one of FVIII and VWF as used herein, including bleeding disorders wherein the cause of the bleeding disorder may be selected from the group consisting of a shortened in vivo half-life of FVIII and/or VWF, altered binding properties of FVIII and/or VWF, genetic defects of FVIII and/or VWF, and a reduced expression of FVIII and/or VWF. In one embodiment of the present invention, the bleeding disorder is selected from the group consisting of hemophilia A, VWD, or other diseases associated with an impaired function of VWF or impaired interaction of VWF with other molecules.

Further, the present invention relates to a pharmaceutical composition comprising an effective amount of a proteinaceous construct as defined above and an effective amount of a complex as defined above. The pharmaceutical composition may further comprise a pharmaceutically acceptable carrier, diluent, salt, buffer, or excipient. The pharmaceutical composition can be used for treating the above-defined bleeding disorders. The pharmaceutical composition of the invention may be a solution or a lyophilized product. There are many known methods of forming stable solutions of proteins, and specifically VWF and FVIII. For example, U.S. Pat. Nos. 6,586,573; 5,565,427; 5,763,401; 5,733,873; 4,877,608; 5,605,884; and 5,328,694. These solutions can be subjected to any suitable lyophylization process, for example, the process described in U.S. Pat. No. 6,586,573, which is herein incorporated by reference. The present invention includes other suitable forms of the polymer-VWF-conjugate either alone or in combination with FVIII.

The figures show:

FIG. 1B shows the carbohydrate residues in VWF which can be bound by at least one polymer molecule.

The present invention will be further illustrated in the following examples, without any limitation thereto.

EXAMPLES

Example 1

Preparation of Polymer—VWF-Conjugate by Modification of Carbohydrate Residues

Figure 1:
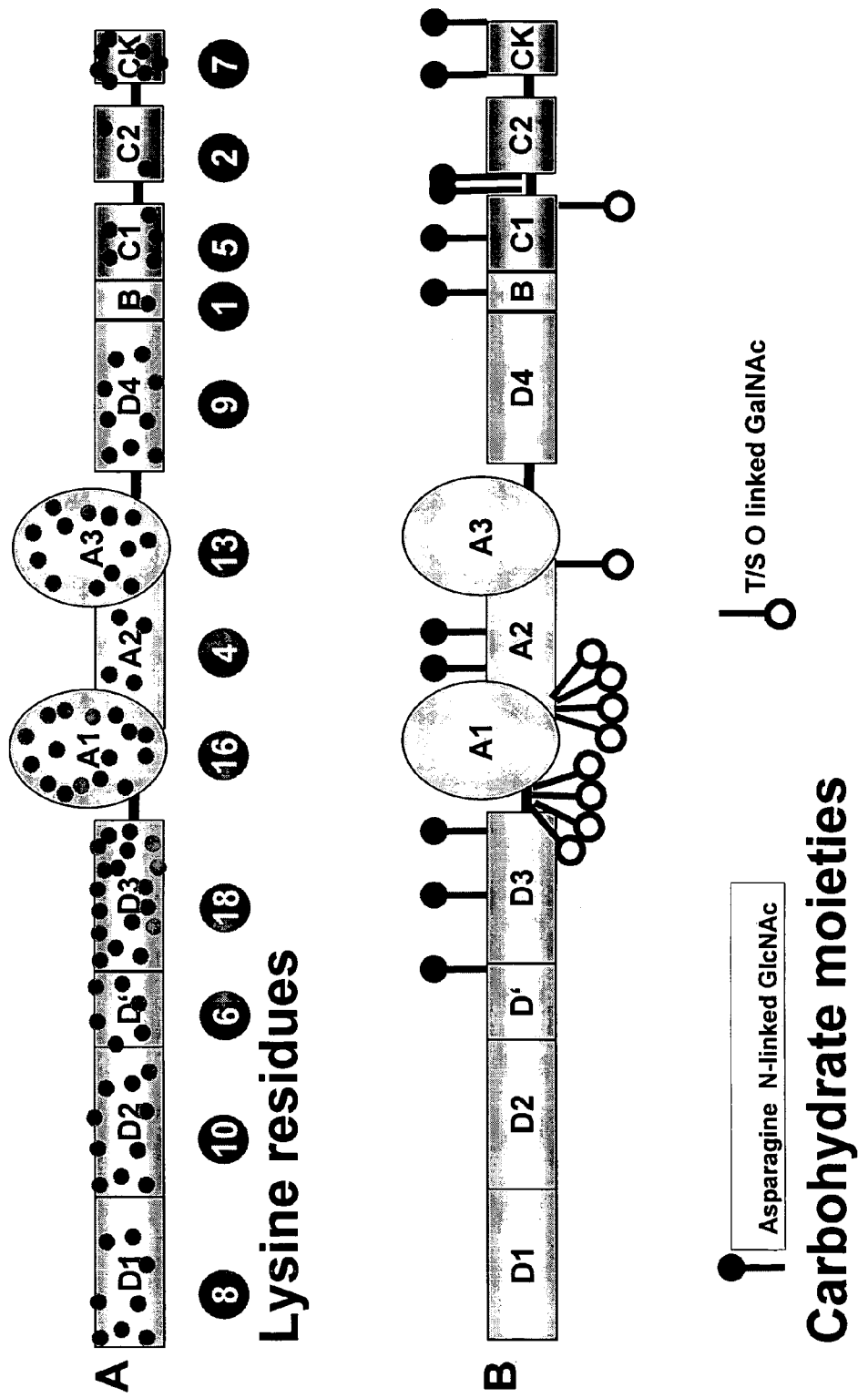
FIGS. 1A and 1B show the schematic structure of VWF/ with examples for target sites for conjugation. The grey dots in FIG. 1A indicate the lysine residues of VWF which can be bound by at least one polymer molecule.

For preparation of polymer—VWF conjugate via carbohydrate residues (FIG. 1B) a solution of rVWF (final concentration: 500 µg/ml) was prepared in 20 mM sodium acetate buffer, pH 6.0 and $NaIO_4$ was added (final concentration 5 mM) for the oxidation of carbohydrate residues. The oxidation was carried out for 20 min at 4° C., then sodium bisulfite (final concentration 5 mM) was added to stop the reaction. Subsequently mPEG-hydrazide (chain length: 3 kD) was added (final concentration 10 mM) and the PEGylation of the VWF was performed for 1 h at room temperature. Then the PEGylated VWF was purified by size-exclusion chromatography. The reaction mixture was applied onto a chromatographic column (size: 26 mm×840 mm) filled with Sephacryl S-300 HR (Amersham) and the PEGylated VWF was separated from the reagents by using 20 mM HEPES-buffer, 150 mM NaCl, pH 7.4 containing 5% trehalose. The modified VWF was eluted in the void volume as indicated by measurements of VWF-antigen levels and OD 280 nm. The VWF containing fractions were directly applied to an anion-exchange column (size: 10 mm×108 mm) filled with EMD TMAE 650 M (Merck) for further purification. Then the PEGylated VWF was eluted with 20 mM HEPES buffer, containing 5% trehalose and 1000 mM NaCl.

Example 2

PEGylation of Lysine Residues in VWF with mPEG Succinimidyl Succinate

For PEGylation of VWF via lysine residues (FIG. 1A) a solution of rVWF (final concentration: 500 µg/ml) was prepared in 20 mM HEPES-buffer, 150 mM NaCl, pH 7.4, containing 5% sucrose) and mPEG succinimidyl succinate (chain length: 5 kD) was added (final concentration 10 mM). The VWF was PEGylated for 1 h at room temperature. Subsequently the PEGylated VWF was purified by size-exclusion chromatography. The reaction mixture was applied onto a chromatographic column filled with Sephacryl S-300 HR (Amersham) and the PEGylated VWF was separated by the same buffer system used for the PEGylation reaction. The VWF was eluted in the void volume as indicated by measurements of VWF-antigen levels and OD 280 nm. The VWF containing fractions were directly applied to an anion-exchange column (size: 26 mm×840 mm) filled with EMD TMAE 650 M (Merck) for further purification. Then the PEGylated VWF was eluted with 20 mM HEPES buffer, containing 5% sucrose and 1000 mM NaCl.

Example 3

PEGylation of Lysine Residues in VWF with mPEG p-nitrophenyl Carbonate

For PEGylation of VWF with mPEG p-nitrophenyl carbonate a solution of plasma derived VWF (final concentration: 500 µg/ml) was prepared in 20 mM HEPES-buffer, 150 mM NaCl, pH 7.6 containing 5% sucrose) and mPEG p-nitrophenyl carbonate (chain length: 2 kD) was added (final concentration 10 mM). The VWF was PEGylated for 2 h at room temperature. Subsequently the PEGylated VWF was purified by size-exclusion chromatography. The reaction mixture was applied onto a chromatographic column filled with Sephacryl S-300 HR (Amersham) and the PEGylated VWF was separated by the same buffer system used for the PEGylation reaction. The VWF was eluted in the void volume as indicated by measurements of VWF-antigen levels and OD 280 nm.

Example 4

PEGylation of Sulfhydryl Residues in VWF with mPEG Maleimide

For PEGylation of VWF via free SH residues with mPEG maleimide a solution of rVWF (final concentration: 500 µg/ml) was prepared in 20 mM HEPES-buffer, 150 mM NaCl, pH 7.6 containing 4% mannose and 1% trehalose) and mPEG maleimide (chain length: 10 kD) was added (final concentration 10 mM). The VWF was PEGylated for 2 h at room temperature. Subsequently the PEGylated VWF was purified by size-exclusion chromatography. The reaction mixture was applied onto a chromatographic column filled with Sephacryl S-300 HR (Amersham) and the PEGylated VWF was separated by the same buffer system used for the PEGylation reaction. The modified VWF was eluted in the void volume as indicated by measurements of VWF-antigen levels and OD 280 nm.

Example 5

Coupling of Dextran to VWF

A dextran (MW 40 kD) solution of 6 mg/ml was prepared in 20 mM sodium acetate buffer, pH 6.0 and $NaIO_4$ was added (final concentration 10 mM) to generate free aldehyde groups. The oxidation was carried out for 1 h at 4° C. in the dark, then sodium bisulfite (final concentration 5 mM) was added to stop the reaction. The activated dextran was dialyzed against 0.1 M sodium phosphate buffer, pH 7.2, containing 0.15 M NaCl (PBS-buffer). Then 2.4 ml of this solution of activated dextran were added to 10 ml of a solution of rVWF (concentration: 0.6 mg/ml in PBS buffer). To this mixture 5 ml of a sodium cyanoborohydride solution (64 mg/ml in PBS buffer) were added and incubated at room temperature overnight in the dark. Then 3 ml of a 1.0 M TRIS-HCl solution, pH 7.2, were added to block remaining aldehyde groups and incubated for 1 h at room temperature and dialyzed against 20 mM HEPES-buffer, pH 7.4, containing 5% sucrose. Then the dextran coupled rVWF derivative was further purified by size-exclusion chromatography by applying the mixture onto a chromatography column (size: 50 mm×860 mm) filled with Sephacryl S-300 HR (buffer: 20 mM HEPES, 5% sucrose, pH 7.4). The rVWF derivative was eluted in the void volume as indicated by measurements of VWF-antigen levels and OD 280 nm. These fractions were collected and concentrated by ultrafiltration using a 100 kD regenerated cellulose membrane (Millipore).

Example 6

Pharmacokinetics in VWD-Mice

Figure 2:
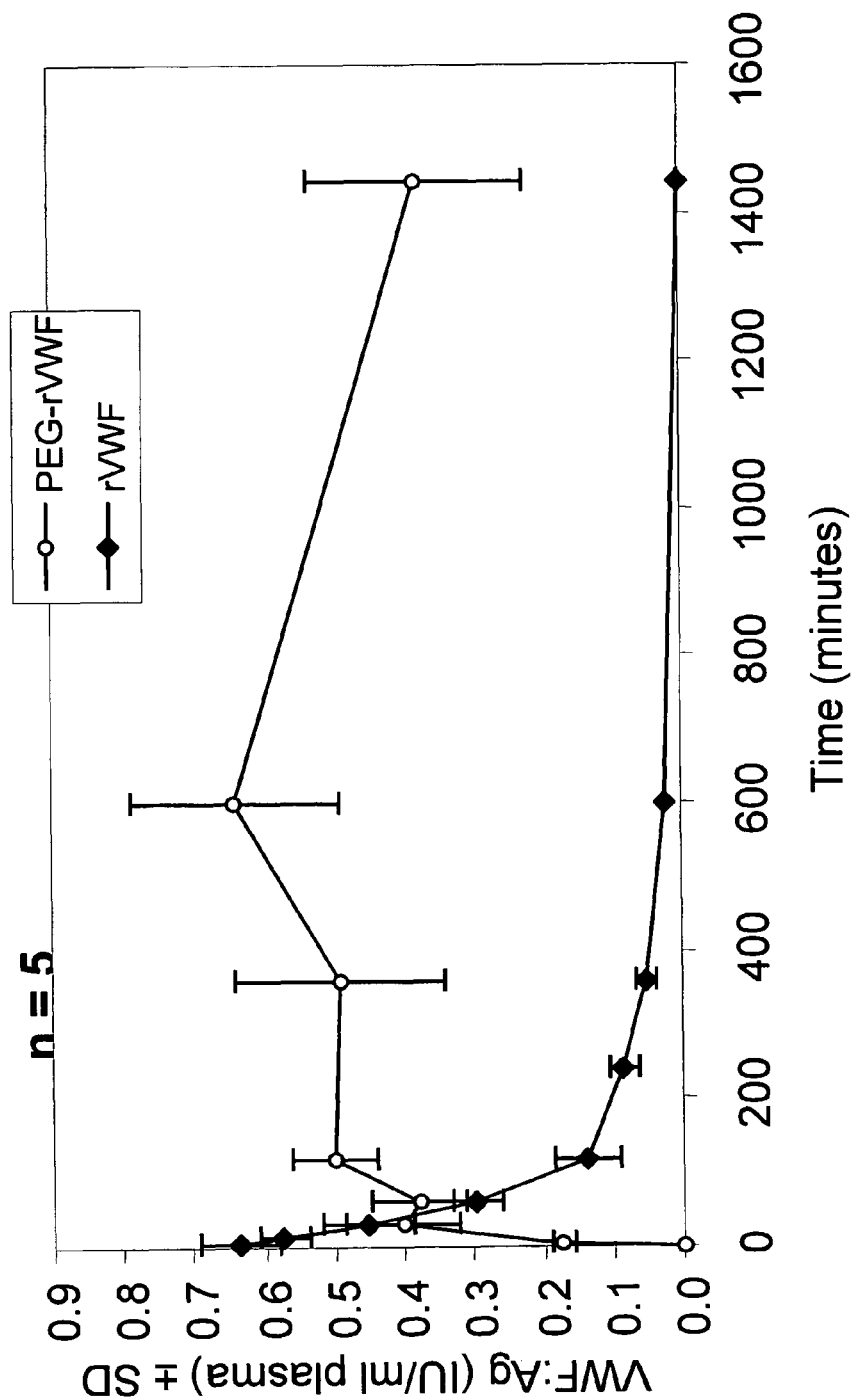
FIG. 2 shows the pharmacokinetics of a polymer-VWF-conjugate compared to non-conjugated VWF in mice with VWD.

VWF-deficient mice described in detail by Denis et al. (PNAS 95: 9524-9529, 1998) were used as a model of human VWD resembling severe type III VWD. Groups of 5 mice received a bolus injection via the tail vein either with PEG-rVWF (chain length 3 kD, PEGylation of rVWF according to Example 1) or native rVWF as control in a dose of 40 U VWF:Ag/kg bodyweight, based on detectable VWF (ELISA) after PEGylation. The PEG-rVWF groups were anesthetized 5 min, 30 min, 1 h, 2 h, 6 h, 10 h and 24 h after injection (5 min, 15 min, 30 min, 1 h, 2 h, 4 h, 6 h, 10 h and 24 h for the control groups) and citrate plasma was prepared from heart puncture. VWF antigen levels were followed in plasma. The results of this experiment are summarized in FIG. 2. Native rVWF is eliminated from the circulation in a typical biphasic manner, as described in the literature (Lenting et al., J. Biol. Chem. 279: 12102-12109, 2004) and falls below the limit of detection between 600 min and 1440 min, equivalent to 10 and 24 h. In contrast, PEGylated rVWF after an initial increase from 0 at the time of injection to approximately 0.6 Upper ml plasma 10 h after injection was still present to a substantially higher level of approximately 0.4 Upper ml even 24 h after injection with a flat decline between 10 h and 24 h indicating a much longer persistence of PEGylated rVWF. The gradual increase in measurable VWF over time indicates the reversibility of the conjugation of the polymer PEG conjugated with VWF, which after release from the polymer becomes accessible for measurement. The long circulation time of PEG-VWF in this model demonstrates that this preparation can be used for the prophylactic treatment of VWD.

Example 7

Pharmacokinetics in FVIII-K.O.-Mice

Figure 3:
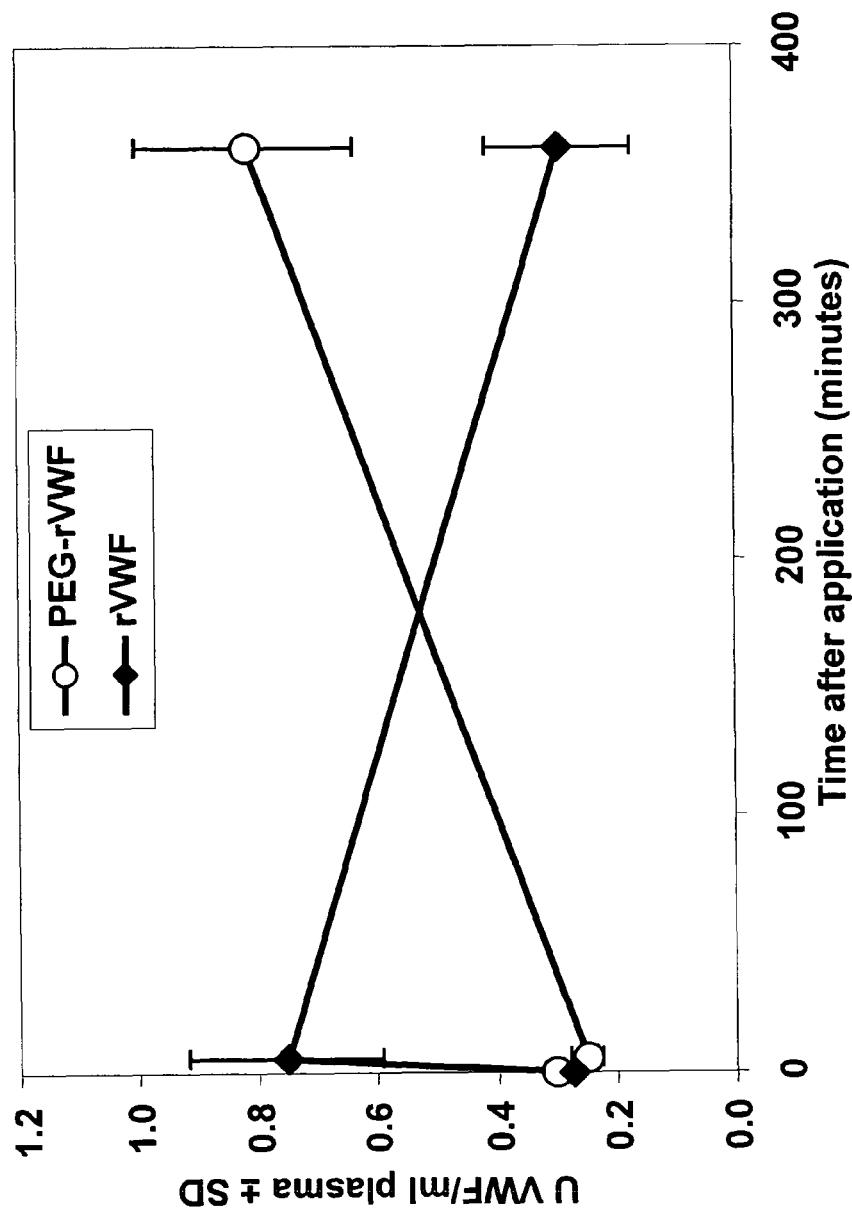
FIG. 3 shows the pharmacokinetics of a polymer-VWF-conjugate compared to non-conjugated VWF in hemophilic mice.

FVIII deficient mice described in detail by Bi et al. (Nat. Genet. 10: 119-121, 1995) were used as a model of severe human hemophilia A. Groups of 5 mice received a bolus injection (13 ml/kg) via the tail vein with either PEG-rVWF (chain length 3 kD, PEGylation of rVWF was performed according to example 1), or native rVWF, each premixed with rFVIII to achieve 3 U FVIII/ml and 3 U VWF:Ag/ml. After anesthesia, citrate plasma was prepared by heart puncture from the respective groups, 5 min and 6 h after product injection. A control group received buffer and was bled 5 min after injection. VWF antigen levels were measured in plasma samples. The results of this experiment are summarized in FIG. 3. The curves indicate a typical elimination for rVWF dropping to near base-level of VWF, present in FVIII deficient mice, whereas after application of PEGylated rVWF, levels increased within the observation period of 6 h. This again indicates the reversibility of the conjugation of the polymer PEG conjugated with VWF, which after release from the polymer becomes accessible for measurement and persists to increase even after 360 min (6 h) following application.

Example 8

FVIII Increase in VWD-Mice

Von Willebrand deficient mice described in detail by Denis et al. (PNAS 95: 9524-9529, 1998) were used as a model of human VWD resembling severe type III VWD. Groups of 4-5 mice were treated intravenously via the tail vein with PEG-rVWF (chain length 5 kD, PEGylation of rVWF was performed according to Example 2) in 20 mM HEPES, 150 mM NaCl, 5% saccharose pH 7.4 or with native rVWF. A control-group was treated with buffer. (PEG-rVWF-dose 18 U VWF:Ag/kg based on ELISA, 2700 µg/kg, rVWF native dose: 2400 µg/kg).

Figure 4:
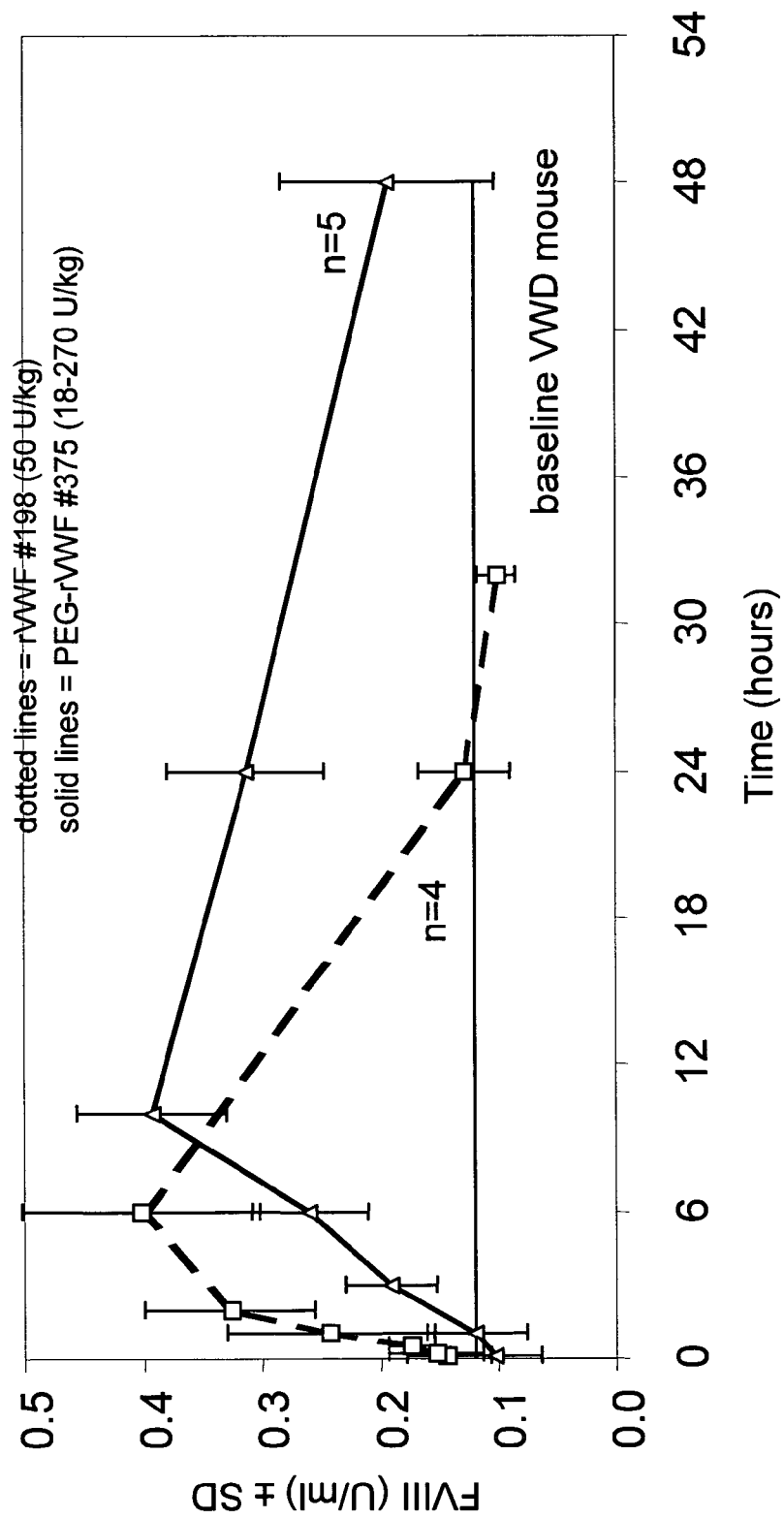
FIG. 4 shows the pharmacokinetics of FVIII in VWD mice treated with rVWF or PEG-rVWF.

Each mouse received a volume dose of 10 ml/kg. At time points after injection of PEG-rVWF (5 min, 1 h, 3 h, 6 h, 10 h, 24 h and 48 h) or native rVWF (5 min, 15 min, 30 min 1 h, 2 h, 6 h, 24 h and 32 h), groups of 4-5 mice were anesthetized, citrate plasma was prepared from heart puncture and the level of FVIII activity (chromogenic in house assay) was followed in plasma. The control-group was bled 15 minutes after injection. The results of this experiment are summarized in FIG. 4.

The level of endogenous FVIII in mice increases as a result of rVWF infusion. The area under curve (AUC) after application of PEGylated rVWF was 8.0 U*h/ml compared to only 3.3 U*h/ml after application of rVWF. This indicates a substantially longer circulation time for PEGylated rVWF. The results show that the PEGylated VWF can be used for the prophylactic treatment of secondary FVIII deficiency in VWD.

Example 9

Recovery of rFVIII and VWF in FVIII-K.O.-Mice

Figure 5:
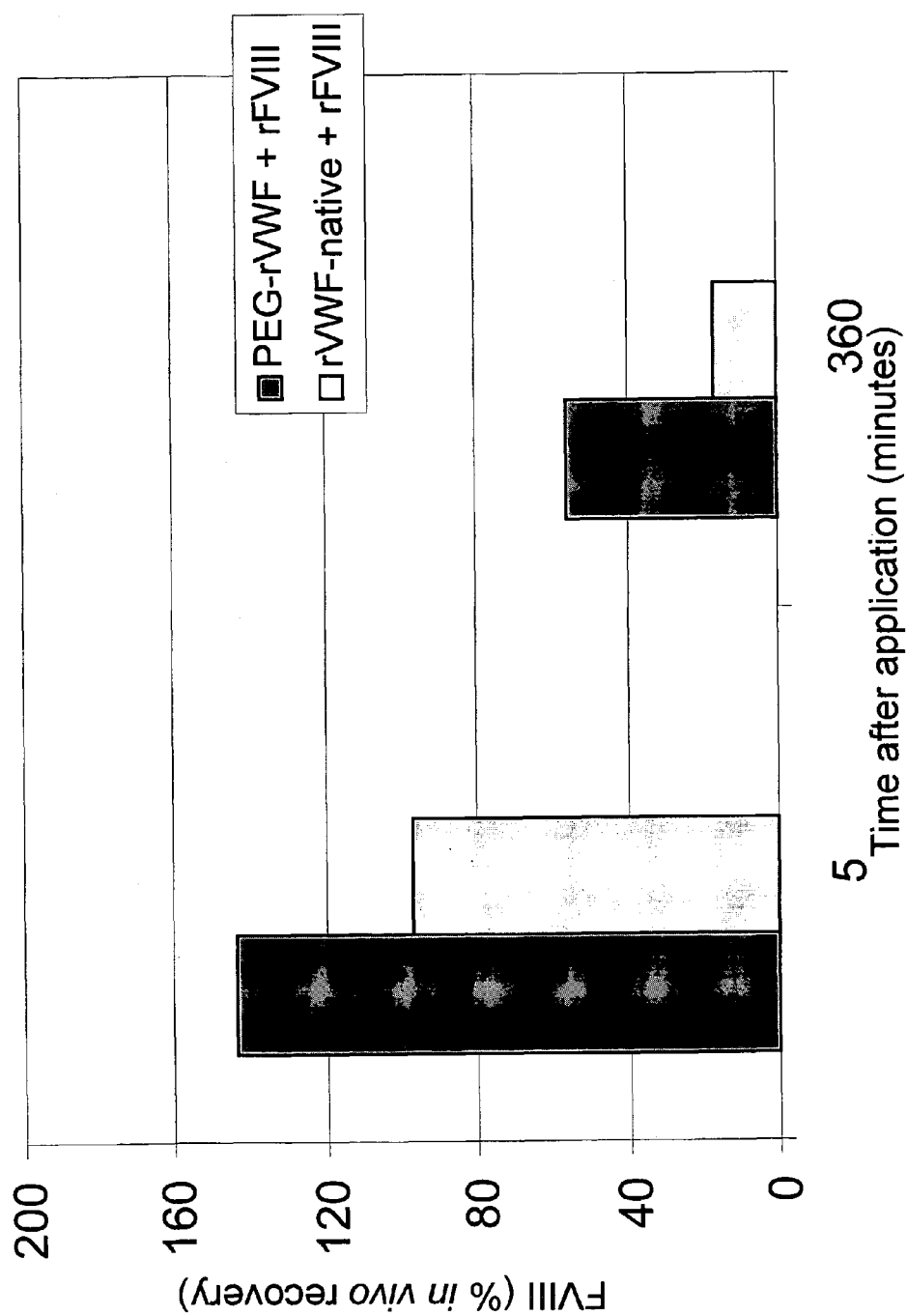
FIG. 5 shows the recovery of rFVIII in hemophilia mice after application of rFVIII complexed with polymer-VWF-conjugate and rFVIII complexed with VWF.
Figure 6:
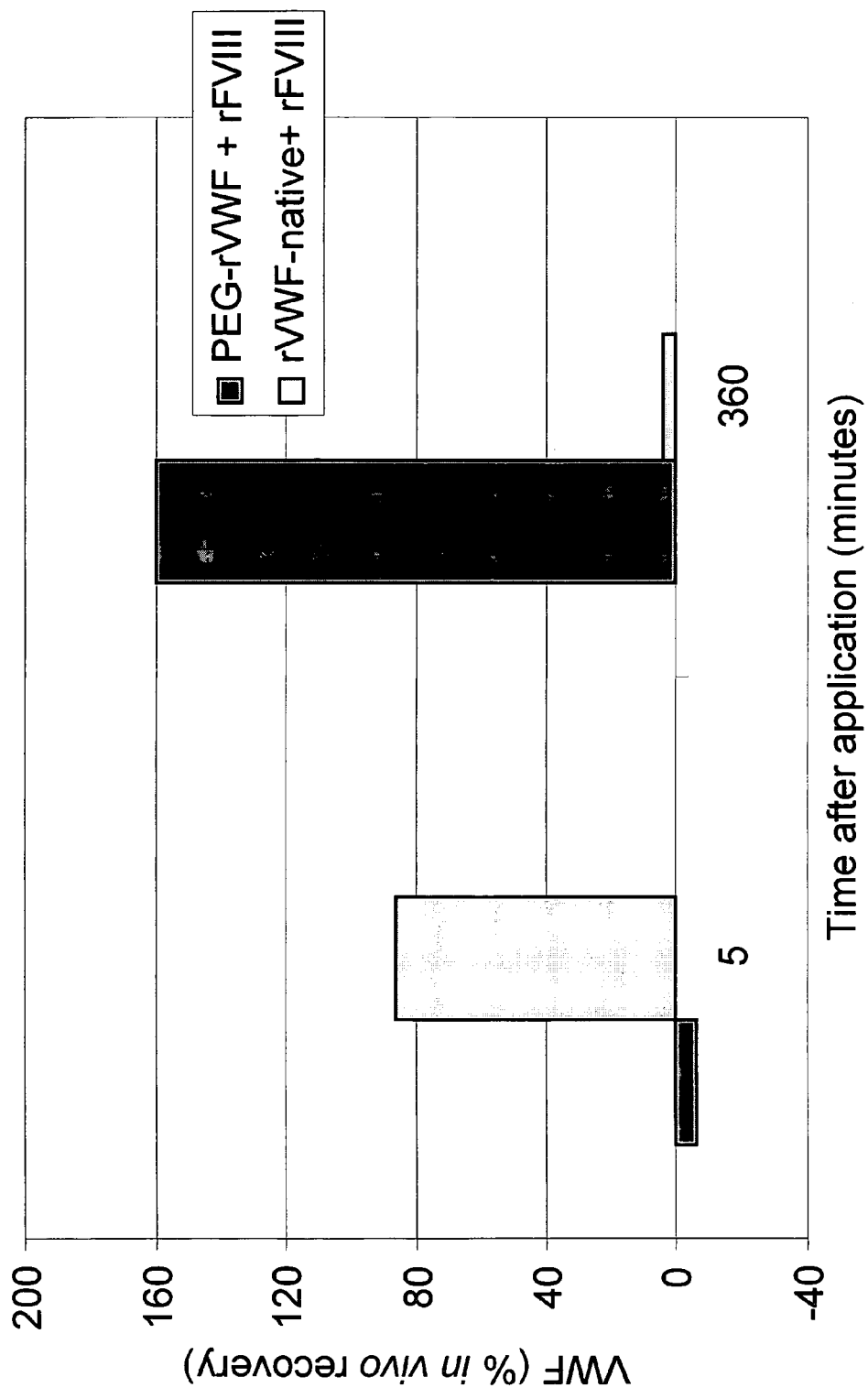
FIG. 6 shows the recovery of VWF in hemophilic mice after application of rFVIII complexed with polymer-VWF-conjugate and rFVIII complexed with VWF.

FVIII deficient mice described in detail by Bi et al. (Nat Genet. 10: 119-121, 1995) were used as a model of severe human hemophilia A. Groups of 5 mice received a bolus injection (13 ml/kg) via the tail vein with either PEG-rVWF (HZ-PEG, 3K, coupled via carbohydrates), or native rVWF, each premixed with rFVIII to achieve 3 U FVIII/ml. Citrate plasma by heart puncture after anesthesia was prepared from the respective groups, 5 min and 6 h after injection. FVIII activity and rVWF antigen recovery levels were measured in plasma samples. The results of this experiment are summarized in FIGS. 5 and 6.

PEGylated rVWF for both preparations induced a higher recovery of co-injected rFVIII, compared to untreated rVWF. The VWF levels increased for PEGylated rVWF over time, while normal rVWF was eliminated almost completely within 360 min. The results show that the PEGylated VWF complexed with FVIII can be used for acute treatment of hemophilia A with the benefit of increased FVIII circulation time.

Example 10

Increase of FVIII Half-Life in FVIIIxVWF-Double Knockout Mice

FVIIIxVWF double knockout mice were obtained by cross-breeding of FVIII deficient and VWF-deficient mice. Those mice suffer from FVIII deficiency as well as from VWF deficiency, thus providing an ideal model for studying FVIII-VWF interactions in an animal model.

Groups of 5 FVIIIxVWF double knockout mice (FVIII deficient mice were crossbred with VWF-deficient mice) received a bolus injection (11 ml/kg) via the tail vein with either PEG-rVWF (chain length 5 kD, PEGylation of rVWF was performed according to example 2 by modification of lysine residues with mPEG succinimidyl succinate) in 20 mM HEPES, 150 mM NaCl, 5% saccharose pH 7.4 or with native rVWF SS-PEG, or native rVWF, each premixed with rFVIII to achieve 9 U FVIII/ml and 9 U VWF antigen/ml and 0.67 U VWF:RCo/ml. The UVF-antigen values were measured by use of an ELISA method as published (Ingerslev, Scand. J. Clin. Invest. 47: 143-149, 1987). The functional VWF:RCo activity reflecting the platelet binding properties of the VWF in the process of primary hemostasis was measured according to Macfarlane et al. (Thromb. Diath. Haemorrh. 34: 306-308, 1975). Five min, 3 h, 6 h, 10 h and 24 h after injection, citrate plasma by heart puncture after anesthesia was prepared from the respective groups. FVIII activity and VWF antigen levels were measured in plasma samples.

Figure 7:
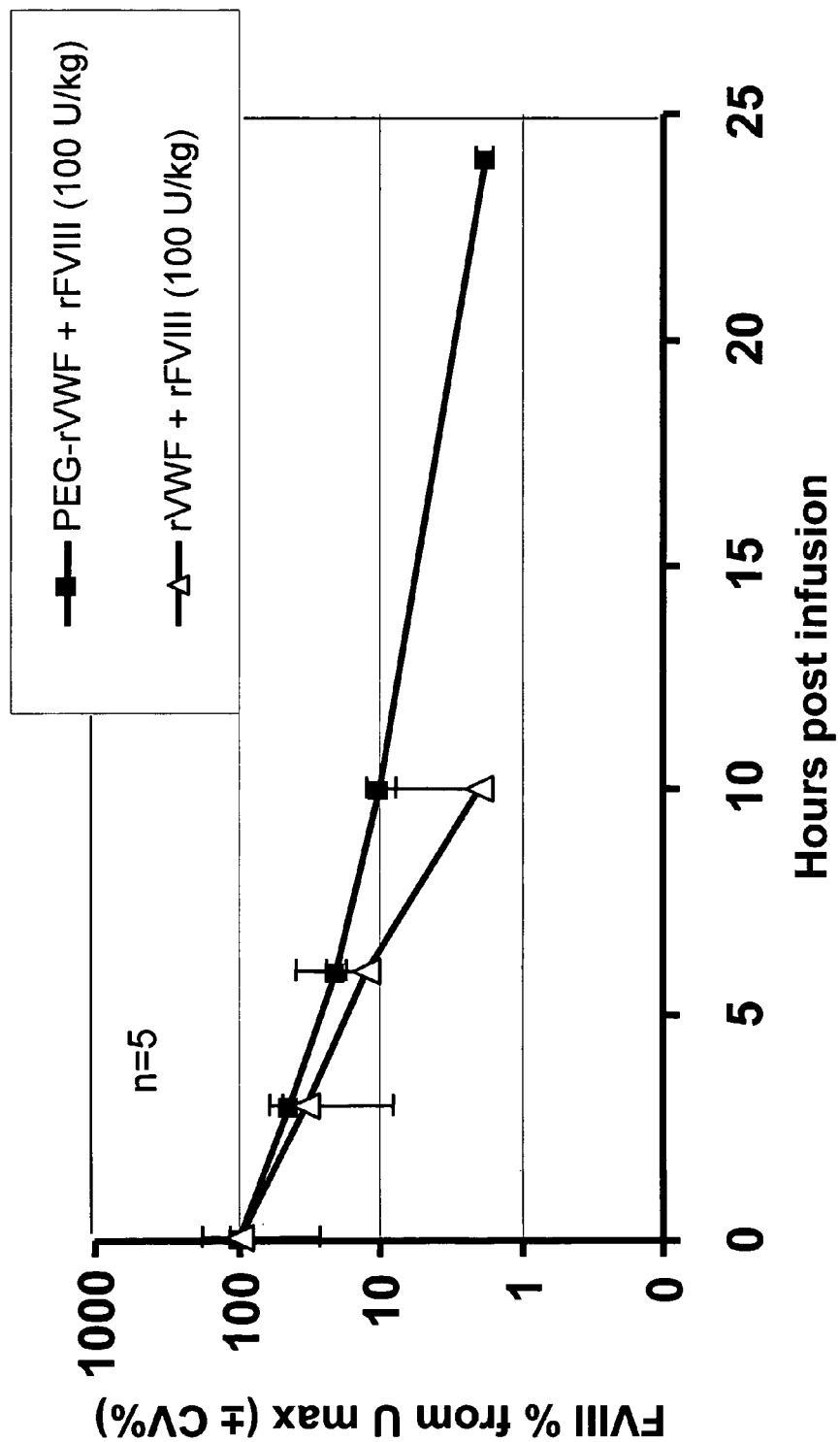
FIG. 7 shows the pharmacokinetics of rFVIII and PEG-rVWF in FVIII×VWF double knockout mice.
Figure 8:
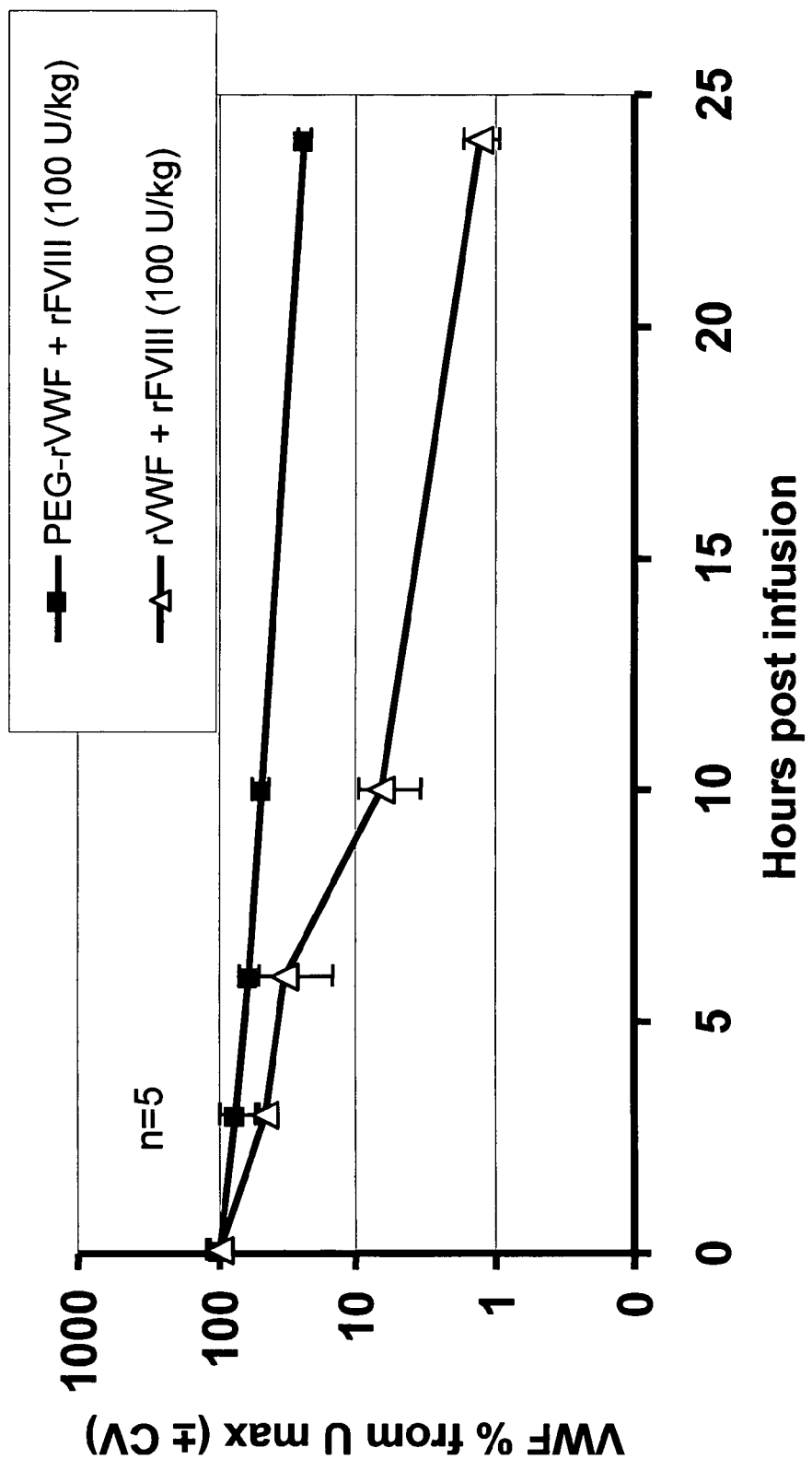
FIG. 8 shows the pharmacokinetics of rFVIII and PEG-rVWF in crossbreed-mice.

Half-life of FVIII and VWF was calculated using the MicroMath Scientist program (Micromath Research, Saint Luis, Mo., US) employing one compartment model from the pharmacokinetic library. Half-life for FVIII, co-infused with either rVWF or PEGylated rVWF increased from 1.88 h to 2.58 h, the area under the curve (AUC) increased from 4.3 to 7.3 U*h/ml. The half-life of VWF increased from 3.1 to 10.4, the area under curve is increased from 5.7 to 22.8. The results are summarized in FIGS. 7 and 8. The data show that PEG-VWF can be used for the acute and prophylactic treatment of hemophilia A and VWD with the benefit of long circulation times of VWD and FVIII.

Example 11

Demonstration of Reversibility of PEGylation in Mouse Plasma

Figure 9:
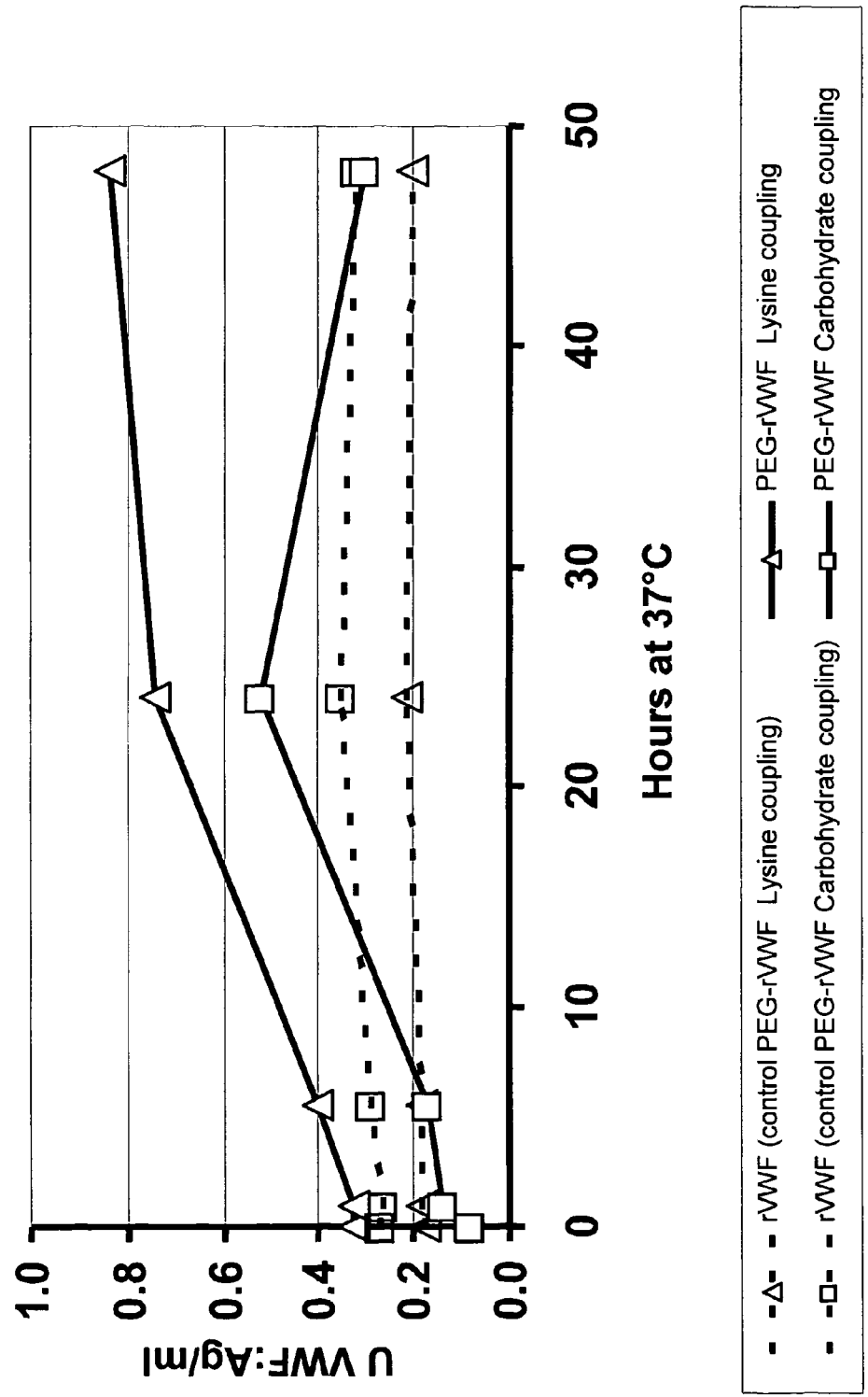
FIG. 9 shows VWF:Ag increase in mouse plasma (lysine and carbohydrate coupling).

The reversibility of PEGylation was demonstrated by in vitro experiments with VWF deficient plasma. Citrated plasma was obtained from VWF-deficient mice (Denis et al. PNAS 95: 9524-9529, 1998) by centrifugation at 1100×g for 15 min at 4° C. Four volumes of mouse plasma were mixed with 1 volume of PEGylated rVWF prepared according to Example 1 (PEG coupling via carbohydrates) or Example 2 (PEG coupling via lysine residues) and kept at 37° C. for 48 h. Non-PEGylated rVWF was used as a control in both experiments. Subsamples were withdrawn immediately after mixing and 1 h, 5.5 h, 24 and 48 h later and the VWF antigen content was assayed from frozen samples by use of a sandwich ELISA system. A polyclonal anti-VWF antibody (DAKO) was used for coating 96 well ELISA plates and a goat-anti-rabbit-IgG-HRP-conjugate (AXELL) was assayed for the detection of bound factor VWF. Over time, increasing amounts of VWF antigen were measured demonstrating the reversibility of conjugation of polyethylene glycol to VWF also in ex vivo plasma samples (FIG. 9).

Example 12

Determination of FVIII Binding Capacity of PEGylated VWF Preparations

Figure 10:
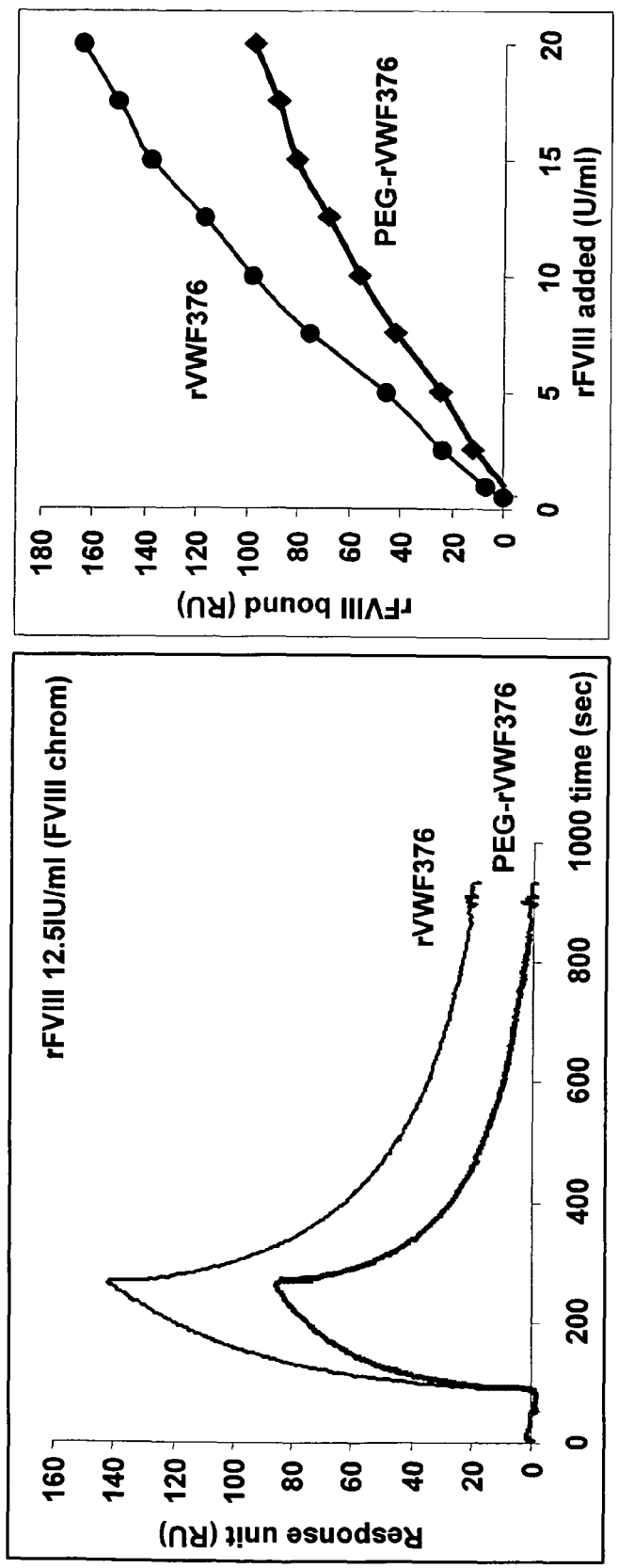
FIG. 10 shows a biomolecular interaction study (left diagram) and comparison of binding capacity of FVIII (right diagram) of PEG-conjugated rVWF compared to non-conjugated rVWF.

The FVIII binding capacity of different PEGylated rVWF-preparations was compared by surface plasmon resonance experiments (Karlsson et Fält, J. Immunol. Methods 200: 121-33, 1997) using a BIACORE®3000 instrument (BIACORE, Uppsala, Sweden). In general, ligands are immobilised to a sensor chip and the binding of other components to the ligand is determined by surface plasmon resonance. By use of this technique the change of the refractive index of the solution close to the surface of the chip is measured. A change in the concentration of a bound component at the surface of the chip is detected as a signal, which is expressed in arbitrary resonance units (RU). There is a linear relationship between the mass of protein bound to the immobilized ligand and the RU observed. The PEGylated VWF preparations were immobilized at 25° C. to the dextran surface of the BIACORE™ sensor chip using NHS/EDC chemistry at 7000-9000 RU and 25° C. A 10 mM HEPES buffer pH 7.4, containing 150 mM NaCl, 3 mM EDTA and 0.005% surfactant P20 (HBS-buffer, BIACORE) was used at a flow rate of 15 µl/min. The binding of different amounts of a commercially available FVIII product (ADVATE, Baxter AG, Vienna, Austria) was measured as illustrated in FIG. 10. This figure demonstrates the FVIII binding capacity of a PEGylated rVWF preparation, modified with mPEG maleimide 5000, prepared according to Example 4. The results of the BIACORE experiments with different PEGylated rVWF preparations are summarized in Table 1. In this table the different FVIII binding capacities of the PEGylated rVWF preparations are given in percent of the RU values of the non PEGylated reference preparation at the maximal level of the reference in the range of 10-20 IU FVIII/ml (chromogenic assay).

TABLE 1

FVIII binding capacities of PEGylated rVWF preparations (non PEGylated rVWF = 100%)

| | Reagent concentration | | | | |
|---|---|---|---|---|---|
| Reagent | 0 mM | 1 mM | 5 mM | 10 mM | 20 mM |
| mPEG SS 5000 | 100% | 30–40% | 20–30% | 0–20% | 0% |
| mPEG MAL 5000 | 100% | 70–90% | 40–60% | 30–50% | 20–40% |
| mPEG Hz 3000 (a) | 100% | 60–80% | 30–50% | 10–20% | 0–5% |

(a) Oxidized with 5 mNaIO$_4$

Example 13

Mass Increase of VWF After Polymer Conjugation rVWF was PEGylated according to Example 2 using mPEG succinimidyl succinate (chain length: 5 kD) in various concentrations (1 mM, 2.5 mM, 5 mM, 7.5 mM and 10 mM). The PEGylated VWF species were analyzed with two different methods: SDS Polyacrylamide gel electrophoresis and VWF multimer analysis. The SDS gel electrophoresis was performed under reducing conditions using a 3-8% gradient gel (Tris Acetat Gel/Bio-Rad). VWF multimer analysis was carried out according to Ruggeri et Zimmerman (Blood 57: 1140-43, 1981) using a 1.6% agarose gel. The visualization of VWF-multimers was carried out according to Aihara et al. (Thromb. Haemost. 55: 263-67, 1986).

Figure 11:
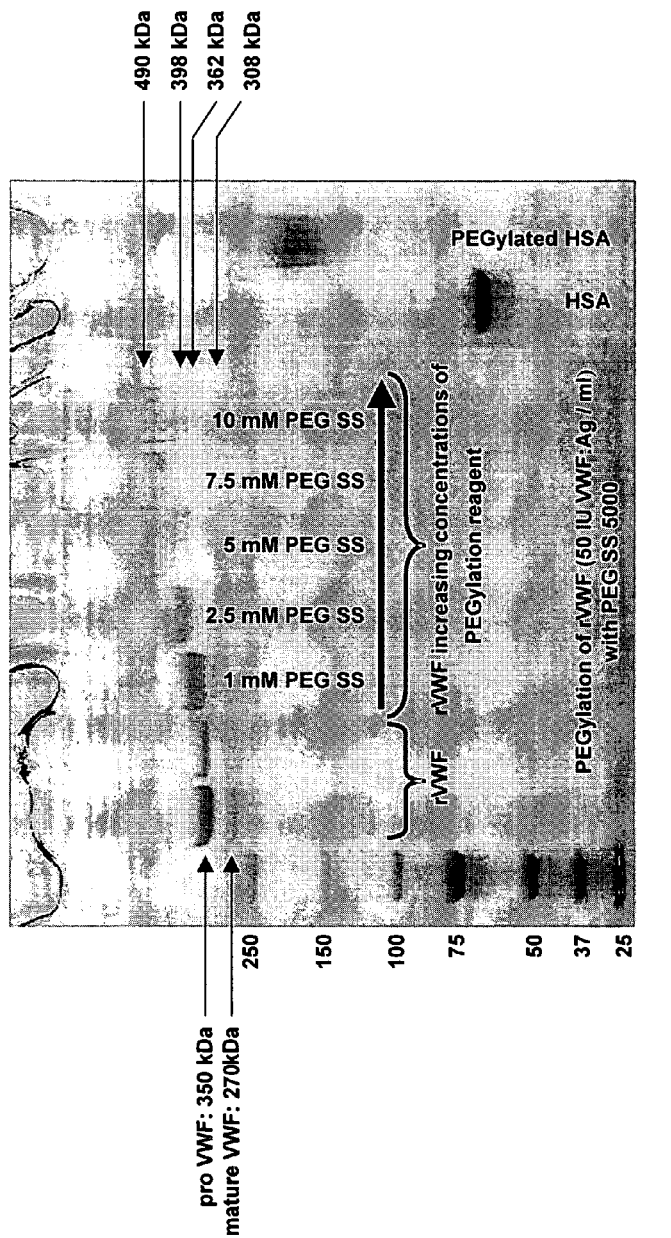
FIG. 11 shows the mass increase of VWF after polymer conjugation measured by SDS-PAGE.
Figure 11:
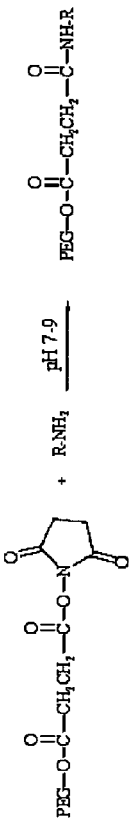

The SDS gel electrophoresis (FIG. 11) shows a rVWF preparation consisting of the mature VWF (lower band) and pro-VWF (upper band) and the increase of the molecular weight after PEGylation by use of different reagent concentrations. In addition the shift of the molecular weight from a human serum albumin (HSA) preparation after PEGylation (PEGylation was carried out according to Example 2 is shown as a reference preparation. It is demonstrated that the molecular weight of HSA is shifting from 66,000 Da to 190,000 Da showing the efficacy of the PEGylation procedure.

Figure 12:
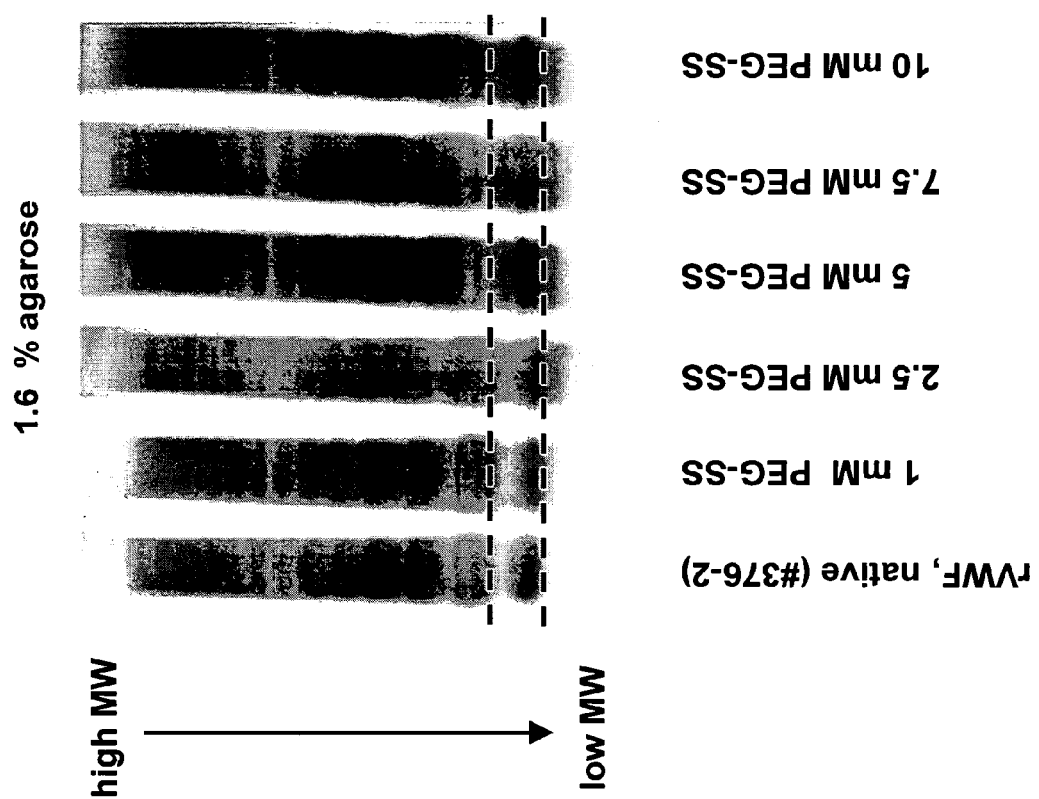
FIG. 12 shows the mass increase of VWF after polymer conjugation measured by agarose electrophoresis to analyze VWF multimers.

FIG. 12 shows the multimeric pattern of rVWF before and after PEGylation with different reagent concentrations. A broadening and a shift to higher molecular weight of the different multimers with increasing reagent concentration is clearly demonstrated.

Example 14

PEGylation of Lysine Residues in VWF with mPEG Succinimidyl Glutarate

For PEGylation of VWF via lysine residues (FIG. 1A) a solution of rVWF (final concentration: 500 µg/ml) was prepared in 20 mM HEPES-buffer, 150 mM NaCl, pH 7.4, 5% sucrose) and mPEG succinimidyl glutarate (chain length: 5 kD) was added (final concentration: 200 mg PEG succinimidyl glutarate/mg protein). Then the pH value was adjusted to 7.4 with 0.1 M NaOH. The VWF was PEGylated for 1 h at room temperature and purified as described in Example 2.

Example 15

Increase of FVIII Half-Life in FVIII-K.O.-Mice

Figure 13:
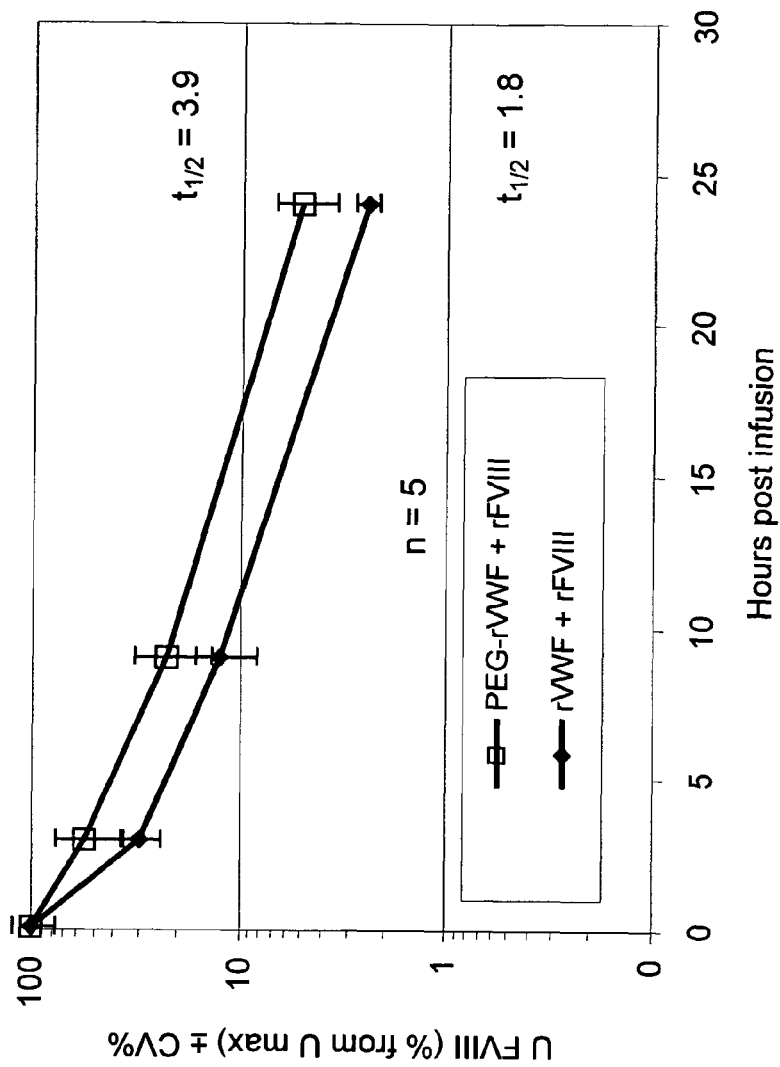
FIG. 13 shows the pharmacokinetics of rFVIII in FVIII-K.O.-mice after application of rFVIII complexed with polymer-VWF-conjugate (rVWF with PEGylated lysine residues) and rFVIII complexed with rVWF.
Figure 14:
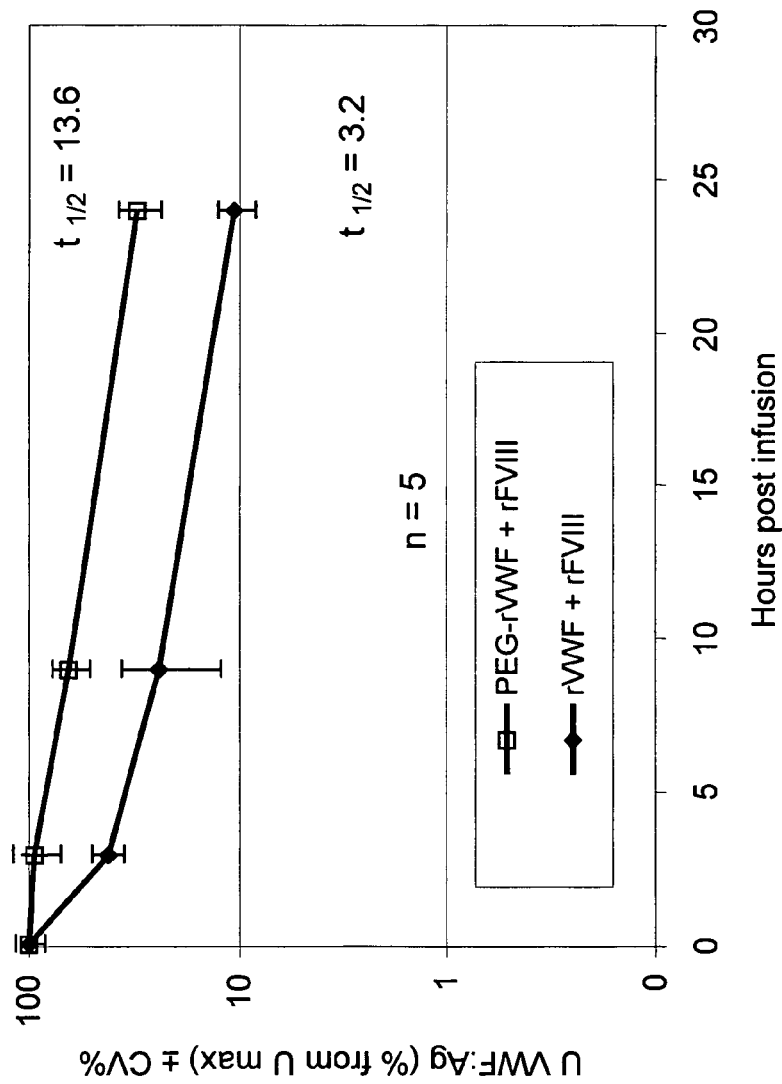
FIG. 14 shows the pharmacokinetics of rVWF in FVIII-K.O.-mice after application of rFVIII complexed with polymer-VWF-conjugate (rVWF with PEGylated lysine residues) and rFVIII complexed with rVWF.

FVIII deficient mice described in detail by Bi et al. (Nat. Genet. 10: 119-121, 1995) were used as a model of severe human hemophilia A. Groups of 5 mice received a bolus injection (10 ml/kg) via the tail vein with either PEG-rVWF (SS-PEG, 5K) prepared according to Example 2 or native rVWF, each premixed with recombinant FVIII to achieve 10 U FVIII/ml and 10 U VWF/ml. Citrate plasma by heart puncture after anesthesia was prepared from the respective groups, 5 min, 3, 9 and 24 h after injection. FVIII activity and VWF antigen recovery levels were measured in plasma samples. The results of this experiment are summarized in FIGS. 13 and 14.

Half-life for FVIII increased from 1.8 h (in the presence of native rVWF) to 3.9 h (when applied together with PEG-rVWF), area under curve (AUC) increased from 4.1 to 7.8 U*h. VWF half-life increased from 3.2 to 13.6 h, AUC for VWF was approximately quadrupled from 7.7 to 32.1 U*h.

Example 16

Figure 15:
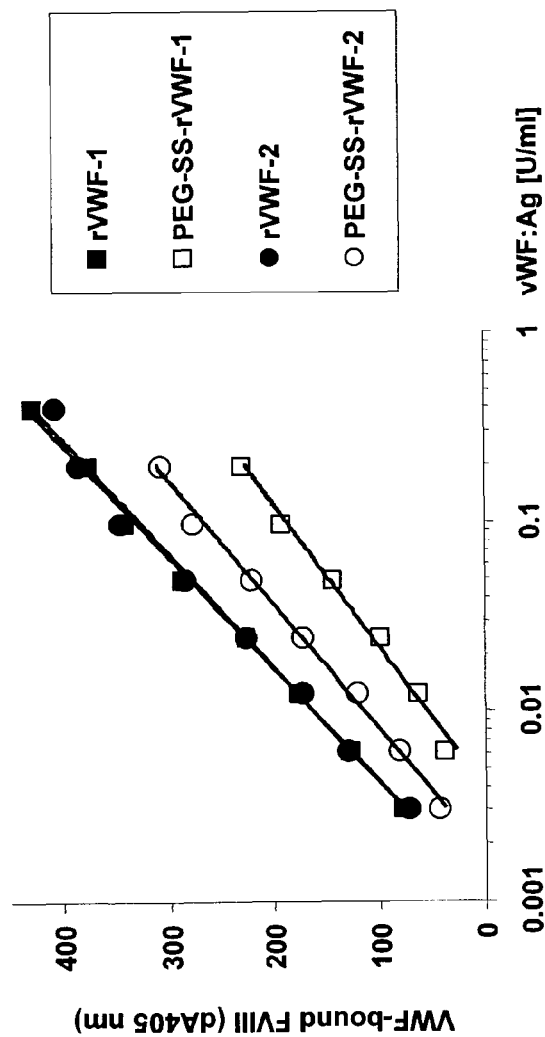
FIG. 15 shows the determination of the FVIII binding capacity of PEG-conjugated rVWF compared to non-conjugated rVWF using a combined ELISA and chromogenic assay (ECA).

Determination of FVIII Binding Capacity of SS-PEGylated VWF Preparations by Different Methods The FVIII binding capacity of different PEGylated rVWF-preparations was measured by a combined ELISA and chromogenic assay system (ECA) using a modification of the method described by Bendetowicz et al. (Blood 92: 529-538, 1998). Microtiter plates were coated with 200 µl of 2.6 µg/mL anti-vWF polyclonal antibody in 50 mmol/l $Na_2CO_3$/$NaHCO_3$, pH 9.6. Plates were subsequently washed after each step with PBS-Tween buffer (100 mM $Na_2HPO_4$/$KH_2PO_4$, 150 mM NaCl, pH 7.6 and 0.05% Tween 20). Plates were blocked for 1 h at 37° C. in 0.1% dry-milk/2 mM benzamidine in PBS-Tween. Increasing amounts of VWF were preincubated for 25 min at 37° C. with 0.2 U/ml rFVIII (ADVATE, Baxter AG, Vienna, Austria), and 100 µl of these mixtures were added to the plates. After incubation, the amount of FVIII bound to the captured VWF was measured by FVIII chromogenic assay (Technoclone, Vienna, Austria). The FVIII binding capacity has been expressed as changes in the absorbance measured at 405 nm (dA405) in 1 min. FIG. 15 shows the VWF dose-dependent FVIII binding of two PEGylated VWF preparations, both modified with mPEG-succinimidyl succinate (SS). The FVIII binding capacity of the modified VWF preparations was calculated as % of the unmodified starting VWF preparations and found to be 20% for PEG-SS-rVWF-1 and 50% of PEG-SS-rVWF-2.

Figure 16:
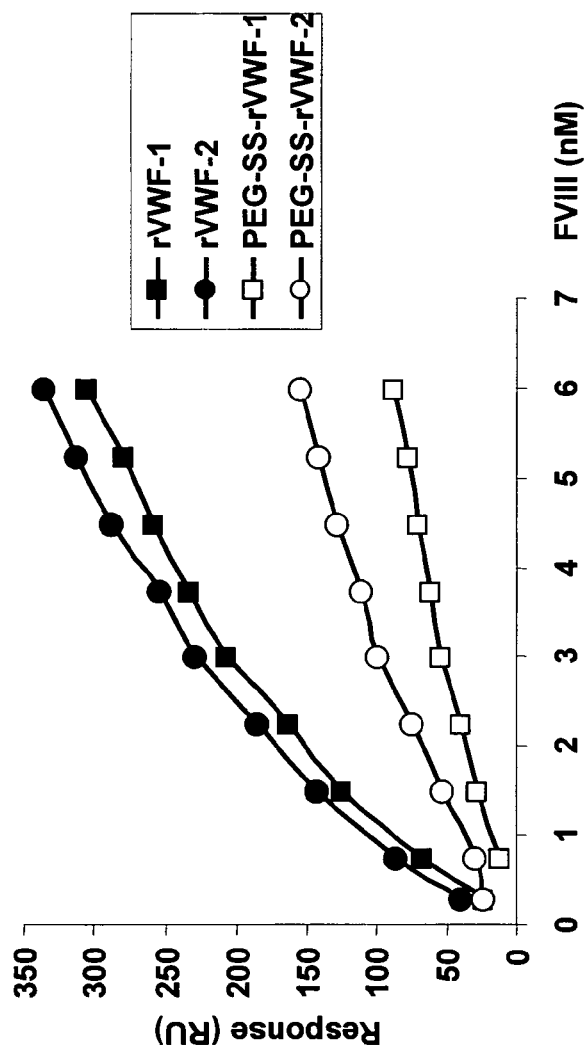
FIG. 16 shows the determination of the FVIII binding capacity of PEG-conjugated rVWF using the surface plasmon resonance technology.

FIG. 16 shows the FVIII binding capacity of the two PEG-SS-rVWF preparations, as measured by the surface plasmon resonance method as described in Example 12. The calculated binding capacity was 25 and 45%, respectively.

Figure 17:
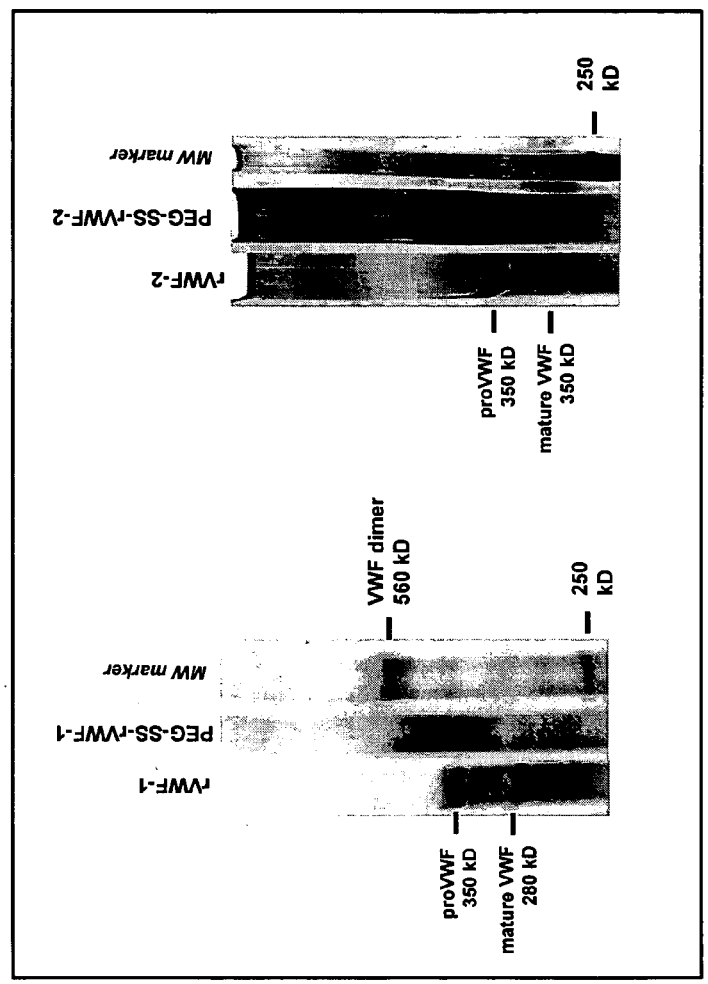
FIG. 17 shows the mass increase of VWF after polymer conjugation measured by SDS-PAGE as described in Example 13.

The appropriate increases in the molecular mass of the rVWF molecule after the PEG-SS conjugation measured by SDS-PAGE are demonstrated in FIG. 17.

Example 17

PEGylation of Sulfhydryl Groups in VWF with Branched PEG Maleimide

For PEGylation of VWF via free SH residues with a branched PEG maleimide a solution of recombinant VWF (final concentration: 500 µg/ml) is prepared in 20 mM HEPES-buffer, 150 mM NaCl, pH 7.6 containing 3% trehalose). Then a branched mPEG maleimide (chain length: 20 kD) supplied by NOF corporation (NOF Europe, Grobbendonk, Belgium) is added (final concentration 10 mM). The VWF is PEGylated for 2 h at room temperature under gentle stirring. Subsequently the PEGylated rVWF is separated from the reagents by ultrafiltration/diafiltration (UF/DF) using a 100 kD membrane consisting of regenerated cellulose (Millipore).

Example 18

PEGylation of Carboxyl Groups in VWF with mPEG Hydrazide/EDC

A furin maturated rVWF is prepared and purified according to Example 23. The preparation is dialyzed against 50 mM phosphate buffer, pH 6.2 and diluted to a concentration of 400

µg/ml. Then mPEG hydrazide (mPEG Hz) with a chain length of 5 kD is added (concentration: 60 mg mPEG Hz/mg VWF). 30 µl of a freshly prepared solution of 500 mM 1-ethyl-3-(3-dimethylaminopropyl) carbodiimide (EDC) is added to 1 ml of the VWF containing mixture and incubated at room temperature under gentle shaking for 5 h. The reagents are separated from the PEGylated rVWF by UF/DF against 20 mM HEPES-buffer (150 mM NaCl, pH 7.4) using a 100 kD membrane (regenerated cellulose/Millipore).

Example 19

Modification of Lysine Residues in VWF with Polysialic Acid

The modification of lysine residues with polysialic acid (colominic acid, CA) was carried out as described by Fernandes et Gregoriadis (Biochim. Biophys. Acta 1341: 26-34, 1997) and Jennings et Lugowski (J. Immunol. 127: 1011-1018, 1981). A solution of colominic acid (concentration: 20 mg/ml) containing 0.1 M $NaIO_4$ was stirred for 15 min in the dark at room temperature to oxidize the CA. Two ml ethylene glycol per ml of the activated CA solution were added and stirred for further 30 min in the dark at room temperature. The solution was dialyzed overnight against 0.05 M sodium phosphate buffer, pH 7.2 in the dark. Subsequently an aliquot of this solution was added to a rVWF solution (400 μg/ml) in 0.05 M sodium phosphate to give a final concentration of 50 mg activated CA per mg VWF. This mixture was stirred for 30 minutes at room temperature in the dark. $NaCNBH_3$ was added (1 mg/mg rVWF) and the mixture was incubated for 18 h at room temperature in the dark under gentle shaking. An aqueous 1 M TRIS-solution, pH 7.2 was added (50 μl per mg $NaCNBH_3$) and stirred for 1 h to terminate the reaction. The free reagents were separated from the rVWF-polysialic acid conjugate by UF/DF using a 100 kD membrane (regenerated cellulose/Millipore).

The FVIII binding capacity of this preparation was determined as described in Example 16.

The conjugation of rVWF with polysialic acid was demonstrated by the shift of the isoelectric point (PI) detected by isoelectric focusing (IEF) under reducing conditions. FIG. 20 shows a comparison of a VWF preparation before and after conjugation with polysialic acid according to this example. The Ampholine PAGplate system (pH 3.5-9.5) was used according to, the instruction of the manufacturer (Amersham Bioscience). The introduction of acidic groups by the conjugation with polysialic acid lead to one single acidic band for the modified rVWF.

A FVIII binding capacity of 54% as described in Example 16 was determined by use of the ECA test. A FVIII binding capacity of 70% was determined using the surface plasmon resonance method (Example 12).

Example 20

PEGylation Under Shear Stress Conditions

A perfusion chamber was manufactured as described by Sakariassen et al. (J. Lab. Clin. Med. 102: 522-535, 1983) and used for the PEGylation of rVWF under shear stress conditions. A solution of rVWF (500 μg/ml) in 20 mM HEPES, pH 7.4 containing 3% trehalose was prepared. Then mPEG succinimidyl succinate (final concentration: 5 mM) is added, the pH value adjusted with 0.1 M NaOH to 7.4 and immediately filled in the perfusion system. Then the PEGylation is carried out at room temperature at a shear rate of 2500 $sec^{-1}$ by use of a peristaltic pump under the perfusion conditions described by Sakariassen et al. (J. Lab. Clin. Med. 102: 522-535, 1983).

Example 21

Preparation of pdVWF

The preparation of pdVWF was carried out according to Thorell et Blombäck (Thromb. Res. 35: 431-450, 1984) with modifications. For preparation of pdVWF, 1.5 kg of cryoprecipitate was dissolved at 20-30° C. in 6 l of water. After stirring for 1 h, the fibronectin precipitate was removed by centrifugation. 8 g NaCl per liter supernatant were added, the solution was warmed to room temperature and SD-stock reagent (1% Tween 80+0.18% acetyltriethylcitrate final concentration) was added for virus inactivation.

The solution was further purified on a EMD-TMAE Fractogel 650 M column (XK50/180) preequilibrated with 0.2M NaCl, 0.02M sodium acetate, pH 6.5 (washing buffer). After washing with 20 column volumes of washing buffer, VWF was eluted with 0.5M NaCl, 0.02M Na-citrate, pH 6.9. For precipitation of VWF glycine (1 M final concentration) and NaCl (3M final concentration) were added. The precipitate was dissolved in buffer and applied onto a Sephacryl S-400 HR (Amersham) column equilibrated in 0.3M $CaCl_2$, 0.15M NaCl, 20 mM HEPES, pH 7.4 for final purification.

TABLE 2

Purification of pdVWF

| Sample | Specific Act. [IU VWF:Ag/ mg protein] | VWF:CB/ VWF:Ag [IU/IU] | VWF:RCo/ VWF:Ag [IU/IU] | VWF:RCo/ FVIII Ag [IU/IU] |
|---|---|---|---|---|
| Starting Material (n = 2) (Cryoprecipitate resuspended) | 1.3 | 0.35 | 0.17 | 0.33 |
| Centrifugation supernatant (n = 2) | 2.3 | 0.34 | 0.19 | 0.39 |
| Fractogel EMD-TMAE 650 M (n = 2) | 191 | 0.72 | 0.47 | 0.77 |
| Sephacryl S-400 HR (n = 2) | 192 | 0.91 | 0.56 | 40 |

Example 22

PEGylation of Lysine Residues in pdVWF with PEG SS

PdVWF was prepared according to Example 21 and diluted with 20 mM HEPES-buffer pH 7.4 (containing 150 mM NaCl and 3% sucrose) to a final concentration of 400 µg/ml. Then mPEG succinimidyl succinate (chain length: 5 kD) was added (concentration: 10 mg PEG SS 5000/mg VWF) and the pdVWF was PEGylated for 1 h at room temperature. Then the reagent was separated from the PEGylated VWF by UF/DF using a 100 kD membrane consisting of regenerated cellulose (Millipore).

Example 23

Furin Maturation and Purification of the Furin-Maturated rVWF 143 kg of the flow-through fraction of an anti-FVIII antibody column derived from a rFVIII fermentation and purification process were treated with furin for removal of the propeptide as described by Schlokat et al. (Biotechnol. Appl. Biochem. 24: 257-267, 1996) and were sterile filtered. The process was based on earlier work (Fischer et al., FEBS Lett. 375: 259-262, 1995; Fischer et al. PCT/AT98/00034[WO 98/38219], 1-33, 1998, 18-2-1998 and Kaersgaard et Barington, J. Chromatogr. B 715: 357-367, 1998).

After 4-fold dilution with water to 16 mS/cm 633 kg of diluted solution were applied on a XK50/15 EMD-TMAE-Fraktogel 650M-column (300 ml gel; Merck; #K14540281) equilibrated with 10 mM Tris, 100 mM NaAc, 86 mM NaCl, pH 6.5, mS/cm (equilibation buffer). The column was washed with equilibration buffer and eluted with 100 mM NaAc, 250 mM NaCl, 100 mM glycine, 3 mM $CaCl_2$.

4506 g of TMAE-eluate were filtered on Sartoclean GF (0.8 & 0.65µ) and Sartobran P (0.45 & 0.2µ), diluted 1.5 fold to 29 mS/cm and pumped through a Mustang Q filter (#IH18770932) for removal of DNA. After SD treatment for 60 min at 22+/−2° C. and 2-fold dilution with water to 16 mS/cm, the solution was applied to an Amicon 70/29 UNO-sphere S-column (600 ml gel; Bio-Rad, #78960C) equilibrated with equilibration buffer of the TMAE step. Column was washed with equilibration buffer and eluted with elution buffer of the TMAE step.

3223 g of UNO-S eluate were concentrated 15 fold by ultrafiltration using a 30 kDa 0.1 $m^2$-membrane (Hydrosart #01080217, Sartorius) consisting of regenerated cellulose. 201 g of the concentrate was finally purified by size exclusion chromatography on a XK50/86.5 Superose 6 Prep Grade column equilibrated with 100 mM NaAc, 500 mM NaCl, pH 7.0 (1698 ml gel; GE Healthcare #17-0489-01).

TABLE 3

Purification of furin-processed rVWF

| Sample | Specific Act. [IU VWF:Ag/ mg protein] | VWF:CB/ VWF:Ag [IU/IU] | CHO/ VWF:Ag [ng/IU] | Purification factor (CHO) | Purification factor per step (CHO) | VWF:RCo/ FVIII Ag [IU/IU] |
|---|---|---|---|---|---|---|
| Starting material (n = 4) | 1 | 0.75 | 23678 | 1.0 | 1 | 0.69 |
| 1.TMAE Eluate (n = 5) | 34 | 0.84 | 2766 | 8.6 | 8.6 | 0.62 |
| Mustang Q (n = 4) | 44 | 0.70 | 2405 | 10 | 1.1 | 0.47 |
| UNO-S Eluate (n = 4) | 121 | 0.71 | 329 | 72 | 7.3 | 0.40 |
| Superose 6 PG (n = 2) | 160 | 0.99 | 4 | 6150 | 85 | 0.39 |

Example 24

PEGylation of Furin-Maturated rVWF

Furin-maturated VWF was prepared according to Example 23 and dialyzed against 20 mM HEPES-buffer pH 7.4 (containing 150 mM NaCl and 3% sucrose). Then the solution was diluted to a final concentration of 300 µg/ml with 20 mM HEPES-buffer pH 7.4 (containing 150 mM NaCl and 3% sucrose). Subsequently mPEG succinimidyl succinate (chain length: 5 kD) was added (concentration: 25 mg PEG SS 5000/mg VWF) and the furin-maturated VWF was PEGylated for 1 h at room temperature. Then the reagent was separated from the PEGylated VWF by UF/DF using a 100 kD membrane consisting of regenerated cellulose (Millipore).

Example 25

In vitro Characterization of the Furin-Maturated rVWF

The FVIII binding capacity of the furin-maturated rVWF was determined by surface plasmon resonance technology and by ECA, as described in Example 12 and FIG. 15, respectively. The results were compared to an albumin-free plasma-derived VWF preparations prepared according to Example 21.

Figure 18:
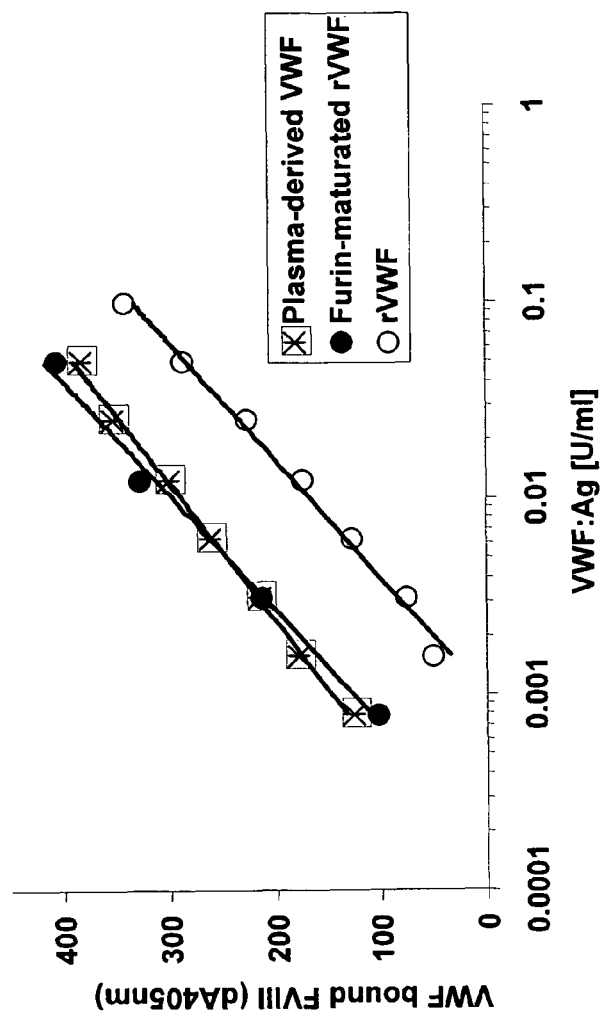
FIG. 18 shows the determination of the FVIII binding capacity of furin-maturated rVWF compared to a pdVWF and non-treated rVWF using a combined ELISA and chromogenic assay (ECA).
Figure 19:
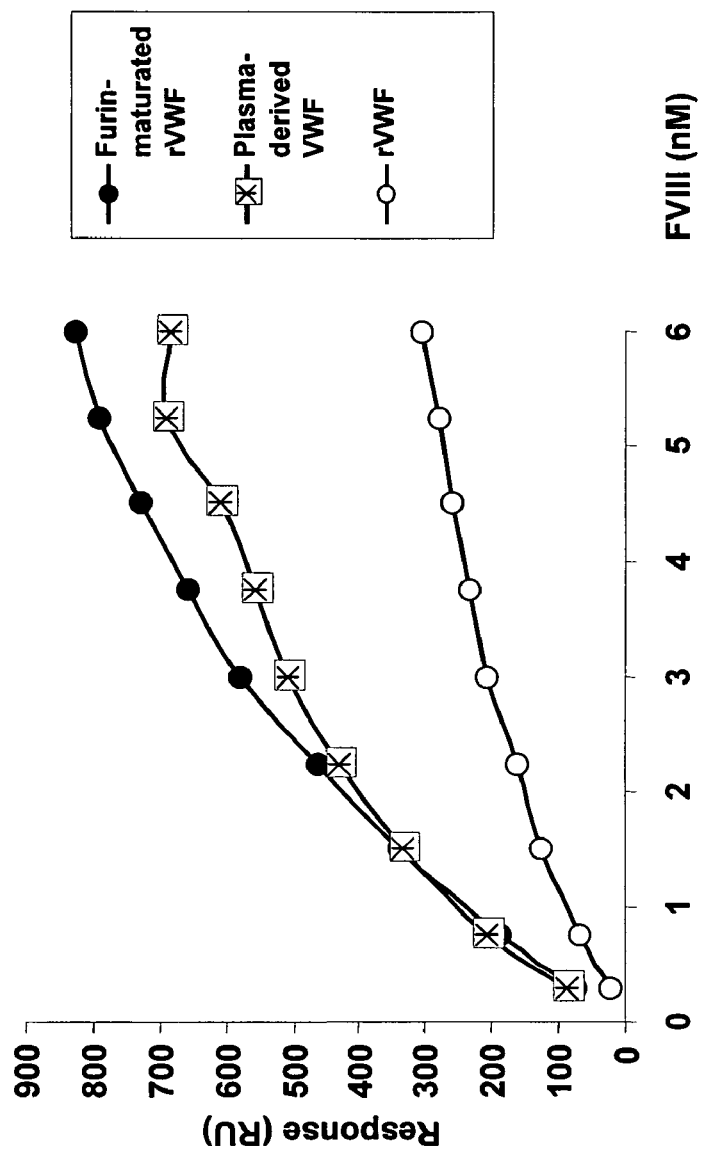
FIG. 19 shows the determination of the FVIII binding capacity of furin-maturated rVWF compared to a pdVWF and non-treated rVWF using the surface plasmon resonance technology.
Figure 20:
FIG. 20 shows the isoelectric focusing patterns of rVWF-polysialic acid conjugate and rVWF under reducing conditions.

As demonstrated in FIGS. 18 and 19, the FVIII binding-capacity of the furin-maturated rVWF was comparable with a plasma-derived reference preparation.

Example 26

Conjugation of VWF with Polysialic Acid by Cross-Linking with Glutaraldehyde For the conjugation of rVWF with polysialic acid (colominic acid) using glutaraldehyde as cross-linking reagent (Migneault et al., Biotechniques 37: 790-796, 2004) 4 ml of a solution of colominic acid (concentration: 20 mg/ml) in 20 mM HEPES-buffer (150 mM NaCl, pH 7.4) are prepared and the pH is adjusted to 7.4 by addition of 0.1 M NaOH. Glutaraldehyde is added to give a final concentration of 0.01%. Subsequently 1 ml of a solution of rVWF (400 µg/ml) in 20 mM HEPES-buffer (150 mM NaCl, pH 7.4) is added in aliquots of 100 µl and the mixture is incubated for 1 h under gentle shaking. Then the mixture is dialyzed, trehalose is added (final concentration: 3%) and the rVWF-polysialic acid conjugate is concentrated by ultrafiltration.

Example 27

Increase of VWF Half-Life in VWF-Deficient Mice

Figure 21:
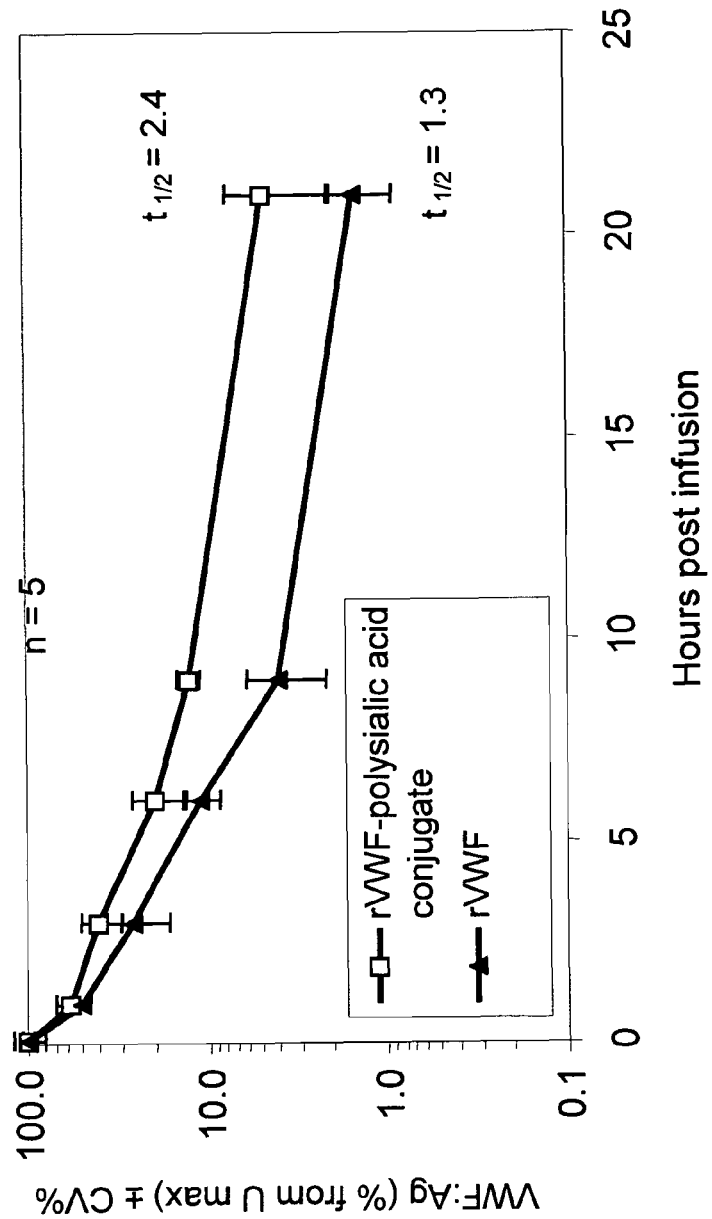
FIG. 21 shows the pharmacokinetics of rVWF-polysialic acid conjugate and rVWF in VWF-deficient mice.
Figure 22:
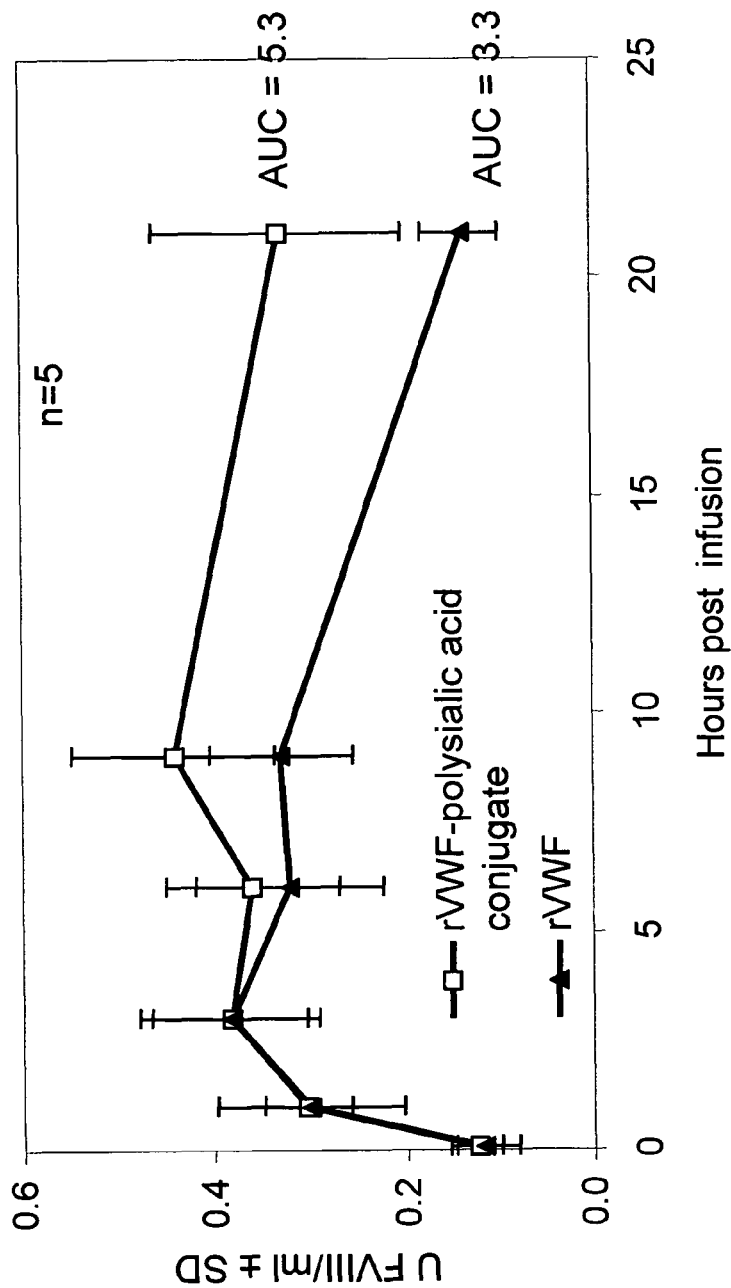
FIG. 22 shows the time course of mouse FVIII activity after application of rVWF-polysialic acid conjugate or rVWF in VWF-deficient mice.
Figure 23:
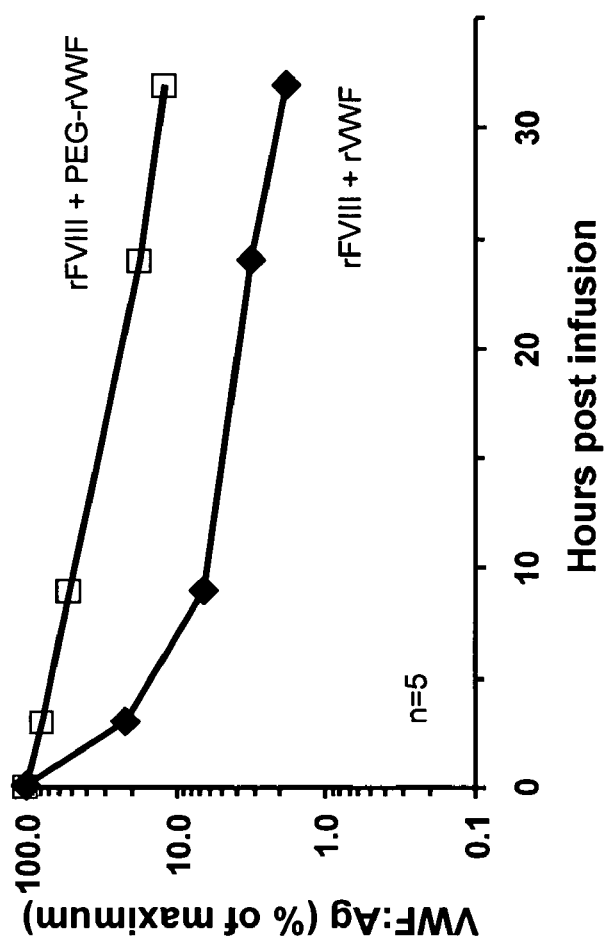
FIG. 23 shows the pharmacokinetics of PEG-rVWF (branched PEG 20K SG) and rVWF in FVIII deficient mice.
Figure 24:
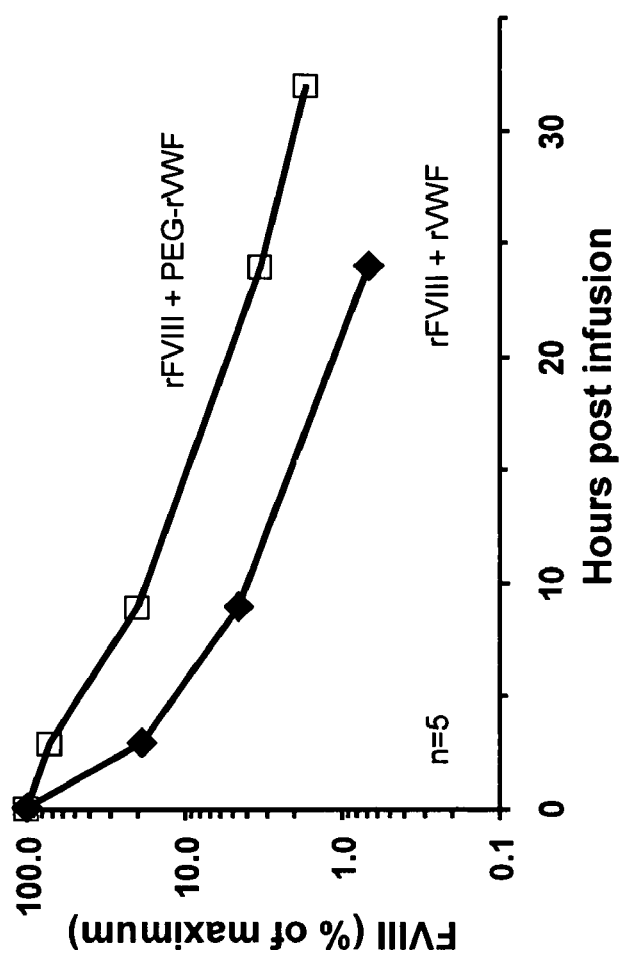
FIG. 24 shows the pharmacokinetics of rFVIII, co-infused with PEG-rVWF (branched PEG 20K SG) or rVWF in FVIII deficient mice.

VWF-deficient mice described by Denis et al. (PNAS 95: 9524-9529, 1998) were used as an animal model of human VWD. Groups of 5 mice received a bolus injection (10 ml/kg) via the tail vein with either rVWF-polysialic acid conjugate prepared according to Example 19 or native rVWF to achieve 100 U VWF:Ag/kg. Citrate plasma by heart puncture after anesthesia was prepared from the respective groups, 5 min, 1, 3, 6, 9 and 21 h after injection. VWF antigen recovery and endogenous mouse FVIII activity levels were measured in the plasma samples. The results of this experiment are summarized in FIGS. 21 and 22.

Half-life of VWF was calculated using the MicroMath Scientist program (Micromath Research, Saint Luis, Mo., US) employing one compartment model from the pharmacokinetic library. Area under curve for FVIII activity was calculated by a trapezoidal model with baseline subtraction.

Half-life of VWF increased from 1.3 h (native rVWF) to 2.4 h (rVWF-polysialic acid conjugate), AUC for FVIII increased from 3.3 U*hr/ml to 5.3 U*hr/ml respectively.

Example 28

Coupling of mPEG Propionaldehyde to Lysine Groups by Reductive Amination

A rVWF solution (400 µg/ml) is prepared in 0.05 M sodium phosphate buffer, pH 7.2 and mPEG propionaldehyde (chain length 5 kDa) is added to give a final concentration of 10 mg mPEG propionaldehyde per mg VWF. This mixture is stirred for 30 minutes. Then NaCNBH$_3$ is added (1 mg/mg rVWF) and the mixture is incubated for 15 h at room temperature under gentle shaking. An aqueous 1 M TRIS-solution, pH 7.2 is added (50 µl per mg NaCNBH$_3$) and stirred for 1 h to terminate the reaction. Subsequently, the PEGylated rVWF is separated from the reagents by ultrafiltration/diafiltration using a 100 kD membrane (regenerated cellulose/Millipore).

Example 29

N-Terminal PEGylation of VWF

N-terminal PEGylation of rVWF is carried out as described by Lee et al. (Pharm. Res. 20: 818-825, 2003). A solution of rVWF (final concentration: 500 µg/ml) is prepared in 50 mM sodium acetate buffer, pH 5.5 and mPEG propionaldehyde (chain length: 5 kD) is added (concentration: 10 mg mPEG propionaldehyde/mg VWF). The PEGylation is carried out for 24 h at room temperature in the presence of 2 mM NaCNBH$_3$ as reducing agent. Subsequently, the PEGylated rVWF is separated from the reagents by ultrafiltration/diafiltration using a 100 kD membrane (regenerated cellulose/Millipore).

Example 30

Sequential PEGylation of Lysine-Residues and SH-Residues of rVWF

RVWF is PEGylated via lysine residues with mPEG succinimidyl succinate (chain length: 5 kD) according to Example 2. The PEGylation is performed at room temperature for 1 h and the free reagents are separated from the rVWF PEG conjugate by UF/DF against 20 mM HEPES-buffer, pH 7.4, containing 5% saccharose using a 100 kD membrane (regenerated cellulose/Millipore). Then the pH value of the solution is adjusted to 7.6 with 0.1 M NaOH and mPEG maleimide (chain length 5 kD/final concentration 10 mM) is added for PEGylation of free SH-groups. The PEGylation is carried out for 2 h at room temperature under gentle shaking. Then the reagents are separated again from the reaction mixture using a 100 kD membrane (regenerated cellulose/Millipore).

Example 31

Enzymatic Oxidation of Carbohydrate Residues and Subsequent PEGylation with PEG-Hz The enzymatic oxidation of carbohydrate residues (Wilchek et Bayer, Meth. Enzymol. 138; 429-442, 1987) in rVWF to create aldehyde groups is carried out as described by Avigad et al. (J. Biol. Chem. 237: 2736-43, 1962) by use of galactose oxidase from *Dactylium dendroides* (Sigma). The solution obtained is dialyzed against 50 mM phosphate buffer, pH 7.2 and diluted to a VWF concentration of 400 µg/ml. Then mPEG hydrazide (mPEG Hz) with a chain length of 5 kD (final concentration: 40 mg mPEG-Hz/mg VWF) is added. The mixture is incubated at room temperature under gentle shaking for 3 h. The reagents are separated from the PEGylated rVWF by UF/DF against 20 mM HEPES-buffer (150 mM NaCl, pH 7.4) containing 5% saccharose using a 100 kD membrane (regenerated cellulose/Millipore).

Example 32

PEGylation of rVWF with Blocking of the FVIII Binding Site by rFVIII

For preparation of PEGylated rVWF with unmodified FVIII binding site 3 ml of a solution containing rFVIII (200 U/ml) and rVWF (40 U VWF:Ag/ml) in 50 mM HEPES-buffer (50 mM HEPES, 150 mM NaCl, 2% trehalose, pH 7.4) are prepared and incubated for 1 h at 37° C. The mixture is cooled to room temperature and PEG succinimidyl succinate (PEG-SS/chain length: 5 kD) is added (final concentration: 1 mg PEG-SS/U VWF:Ag) and incubated for 1 h under gentle shaking. Then CaCl$_2$ is added under gentle shaking to give a final concentration of 400 mM. This solution is applied onto a chromatographic column (2.6×80 cm) filled with Sephacryl S-400 HR (Amersham) and the PEGylated rVWF with a free binding site for FVIII is separated from the rFVIII by size-exclusion chromatography (elution buffer: 50 mM HEPES-buffer, 400 mM CaCl$_2$, pH 7.4).

Example 33

Figure 25:
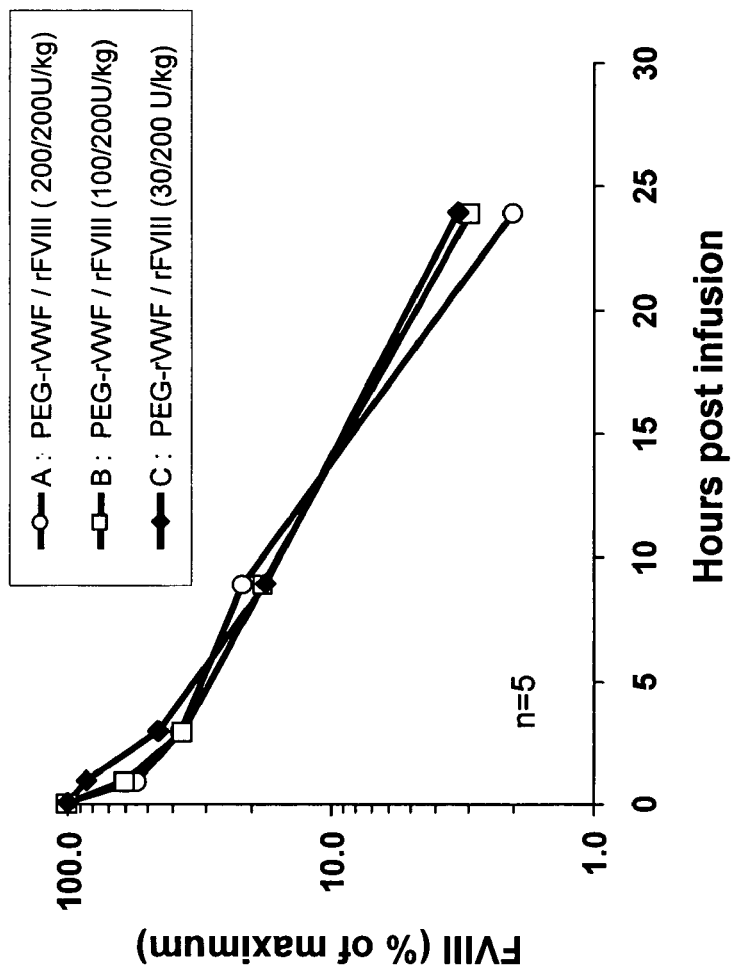
FIG. 25 shows the pharmacokinetics of rFVIII, co-infused with various amounts of PEG-rVWF (branched PEG 20K SG) in FVIII deficient mice.

PEGylation of rVWF with Blocking of the FVIII Binding Site by Heparin 5 ml of a solution of rVWF (300 µg/ml) in 50 mM HEPES-buffer, pH 7.4 are prepared and added to 2 ml of a suspension of Heparin-Sepharose CL-6B (Amersham Bioscience) in the same buffer. This mixture is incubated for 2 h under gentle shaking and the VWF is bound to the gel (de Romeuf et Mazurier, Thromb. Hamost. 69: 436-440, 1993). Subsequently mPEG succinimidyl succinate (200 mg/mg VWF) is added to the mixture and the PEGylation is carried out at room temperature under gentle shaking for 1 h. The mixture is diluted with an equal volume of HEPES-buffer, pH 7.4 containing 2M NaCl. The gel is separated from the supernatant by filtration. Then the gel is washed 3× with 2 ml HEPES-buffer, pH 7.4 (20 mM HEPES, 1 M NaCl) and the supernatant and the washing solutions are combined. Subsequently the solution containing the PEGylated VWF is concentrated by ultrafiltration and diafiltrated against 20 mM HEPES-buffer, pH 7.4 (150 mM NaCl, 3% saccharose) using a 100 kD membrane consisting of regenerated cellulose (Millipore). The derivative obtained shows full FVIII binding capacity by use of the Biacore technology or the ECA test (the test systems are described in U.S. Provisional Patent Application Ser. No. 60/668,378 filed Apr. 4, 2005).

Example 34

Conjugation of VWF with Hyaluronic Acid

The modification of lysine residues with hyaluronic acid (HA) was carried out by reductive amination using hyaluronic acid from Sigma (C 53747). HA was dissolved in a freshly prepared 0.1 M $NaIO_4$ solution to give a final concentration of 5 mg HA/ml. Then the oxidation was carried out for 15 min in the dark under gentle stirring. The reaction was stopped by the addition of 2 ml ethylene glycol per ml oxidized HA solution and further stirring for 30 min in the dark at room temperature. The solution was dialyzed over night against 0.05 M sodium phosphate buffer, pH 7.2 in the dark at 4° C. Subsequently an aliquot of this solution was added to a rVWF solution (40 U VWF:Ag/ml) in 0.05 M sodium phosphate buffer, pH 7.2 to give a final concentration of 50 mg activated HA per mg protein. This mixture was stirred for 120 min at room temperature in the dark. $NaCNBH_3$ was added (1 mg/mg protein) and the mixture was incubated for 18 h at room temperature in the dark under gentle shaking. Then 100 μl 1 M Tris-buffer, pH 7.2 was added per ml of this mixture and stirred for 1 h to terminate the reaction. The free reagents were separated from the rVWF HA conjugate by UF/DF using a 100 kD membrane (regenerated cellulose/Millipore).

Example 35

Biochemical In Vitro Characterization of PSA Conjugated VWF

RVWF was polysialylated according to Example 19. In addition to the parameters described in this example such as isoelectric focusing (FIG. 20), the determination of FVIII binding capacity by the ECA-test (54%) according to Example 16 and by surface plasmon resonance (70%) according to Example 12 the ratio VWF:RCoNWF:Ag was calculated. The VWF antigen level was determined by use a commercially available assay system (Asserachrom vWF, Roche, Basel, Switzerland). The functional activity of the preparation was determined by the Ristocetin Co-factor assay as described by Macfarlane et al. (Thromb. Diath. Haemorrh 34: 306-308, 1975). The ratio of 0.39 calculated for the rVWF starting material decreases to 0.13 after polysialylation.

Example 36

Conjugation of rVWF with Branched PEG Via Lysine Residues

A solution of a mature rVWF (35 U VWF:Ag/ml) in 20 mM HEPES buffer, 150 mM NaCl, pH 7.4, containing 0.5% sucrose was prepared according to Example 23. Then branched mPEG succinimidyl glutarate (PE-SG/chain length: 20 kD) supplied by NOF corporation (NOF Europe, Grobbendonk, Belgium) was added to this solution under gentle stirring (5 mg PEG-SG/mg protein) and the pH value was adjusted to 7.4 by drop wise addition of 0.5 M NaOH. Then the PEGylation was carried out under gentle stirring for 1 h at room temperature. Subsequently the reaction mixture was applied onto an equilibrated ion-exchange chromatography resin (Fractogel EMD TMAE 650M) in 20 mM HEPES buffer, 150 mM NaCl, pH 7.4, containing 0.5% sucrose. Then the column was washed with 20 CV equilibration buffer to remove excess reagent and the PEGylated rVWF was eluted with elution buffer (20 mM HEPES, 0.5 M NaCl, 0.5% sucrose, pH 7.4). The eluate was concentrated by ultrafiltration/diafiltration with a membrane consisting of regenerated cellulose and with a molecular weight cut-off of 100 kD using a buffer system consisting of 20 mM HEPES, 150 mM NaCl, 0.5% sucrose, pH 7.4. The PEGylated derivative obtained showed a slightly diminished VWF:RCoNWF:Aa ratio of 0.79 as compared with the rVWF starting material (VWF: RcoNWF:Ag ratio: 0.89). In addition, the PEGylated rVWF starting material had a FVIII binding capacity of 83% as measured by the ECA test (Example 16).

Example 37

Pharmacokinetics of VWF Conjugated with Branched PEG's in FVIII-K.O.-Mice

FVIII deficient mice (Bi et al., Nat. Genet. 10: 119-121, 1995) were used as a model of severe human hemophilia A. Groups of 5 mice received a bolus injection (10 ml/kg) via the tail vein with either a mixture of PEG-rVWF (branched PEG, SG) and rFVIII or a mixture of native rVWF and rFVIII to achieve 30 U FVIII/ml and 25 U VWF/ml. Five min, 3, 9, 24 and 32 h after injection citrate plasma was prepared from the respective groups by heart puncture after anesthesia. FVIII activity and VWF antigen recovery levels were measured in plasma samples. The elimination curves for VWF and FVIII are shown in FIG. 23 and FIG. 24. VWF half-life increased from 1.4 to 9.7 h, AUC for VWF increased from 11.8 to 49.2 U*h/ml. Half-life for FVIII increased from 1.2 h (in the presence of native rVWF) to 4.4 h (when applied together with PEG-rVWF), area under curve (AUC) increased from 12.1 to 30.5 U*h/ml.

Example 38

Comparative Pharmacokinetics of FVIII Mixed with Different Amounts of PEG-VWF in FVIII-K.O.-Mice Groups of 5 FVIII deficient K.O.-mice received a bolus injection (10 ml/kg) via the tail vein with various mixtures of PEG-rVWF (PEGylation of lysine residues with 25 mg branched PEG-SG 20000/mg protein) and rFVIII (A: 20 IU PEG-rVWF/ml+20 IU FVIII/ml; B: 10 IU PEG-rVWF/ml+

20 IU FVIII/ml; C: 3 IU PEG-rVWF/ml+20 IU FVIII/ml). For the PEGylated rVWF a ratio of 3 mole PEG/mole lysine was calculated. Comparing the same quantities (based on units) of PEG-rVWF and rFVIII in the different PEG-rVWF/rFVIII mixtures the following ratios of PEG/FVIII could be calculated: 3:1 (A); 1.5:1 (B): 0.45:1 (C). After anesthesia citrate plasma was prepared by heart puncture from the respective groups 5 min, 1, 3, 9, and 24 h after injection. No relevant difference in FVIII half-life (A: 2.1 h, B: 2.0 h, C, 2.5 h) and AUC (A: 18.9, B: 14.5 and C, 13.2 U*hr/ml) was found. The elimination curves for FVIII are shown in FIG. 25.

Example 39

Figure 26:
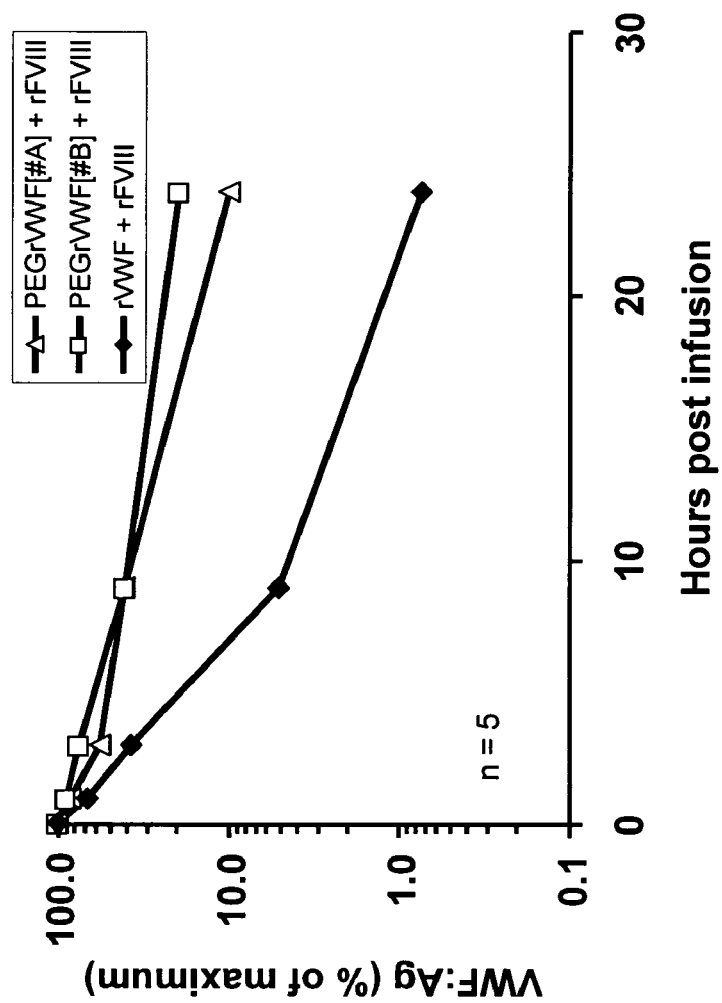
FIG. 26 shows the pharmacokinetics of PEG-rVWF #A (5 mg PEG/mg protein), PEG-rVWF #B (20 mg PEG/mg protein) and native rVWF in FVIII deficient mice.
Figure 27:
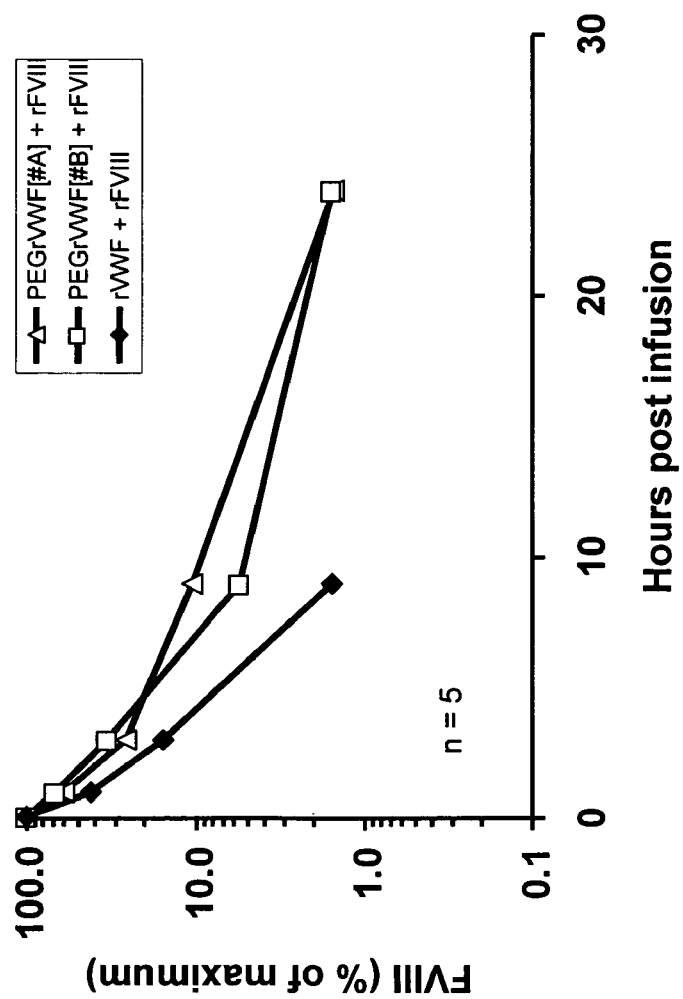
FIG. 27 shows the pharmacokinetics of rFVIII, co-infused with PEG-rVWF #A (5 mg PEG/mg protein), PEG-rVWF #B (20 mg PEG/mg protein) or native rVWF.

Comparative Pharmacokinetics using PEG-VWF Preparations with Different Degrees of PEGylation FVIII×VWF double knockout mice were obtained by cross-breeding of FVIII deficient and VWF-deficient mice. Those mice suffer from FVIII deficiency as well as from VWF deficiency. Groups of 5 FVIII×VWF double knockout mice were infused via the tail vein with a mixture of native rVWF/rFVIII (100/150 IU/kg) or with PEGylated rVWF #A mixed with rFVIII (100/150 IU/kg) or with PEGylated rVWF #B mixed with rFVIII (150/150 IU/kg). PEG-rVWF #A (5 mg PEG-SS 5000/mg protein) and PEG-rVWF #B (20 mg PEG-SS 5000/mg protein) were prepared according to Example 24. For preparation #A a ratio of 2.5 mole PEG/mole lysine and for preparation #B a ratio of 10 mole PEG/mole lysine was calculated. For this citrate plasma samples were prepared 5 min, 1, 3, 9 and 24 h after sample application. Plasma levels of VWF:Ag and FVIII activity were measured and expressed as percent of the maximum plasma level, generally reached 5 min after injection. The elimination curves for VWF and FVIII are shown in FIG. 26 and FIG. 27, respectively. Half-life was 6.3 h and 8.1 h for PEG-rVWF #A and #B respectively. For the native rVWF a half-life of 2.0 h was calculated. The normalized AUC (% of maximum× h) for both PEGylated rVWFs increased from 360%*h (native rVWF) to 901%*h (#A) and 1064%*h (#B). The circulation time for co-infused rFVIII was improved by PEGylated rVWF compared with native VWF. The half-life of FVIII was 0.8 h in the presence of native rVWF, and increased to 1.5 and 1.8 h when infused with PEGylated rVWF #A and #B respectively. The AUC for FVIII was 214, 370 and 358%*h.

Example 40

PEGylation of VWF-Dimer

A solution of a VWF dimer (58 IU VWF:Ag/ml), which was purified from the conditioned medium of a recombinant CHO cell line (Baxter BioScience), was prepared in 20 mM HEPES buffer, 150 mM NaCl, pH 7.4, containing 0.5% sucrose was prepared. Then branched mPEG succinimidyl glutarate (PE-SG/chain length: 20 kD) supplied by NOF corporation was added to this solution under gentle stirring (5 mg PEG-SG/mg protein) and the pH value was adjusted to 7.4 by drop wise addition of 0.5 M NaOH. The PEGylation was carried out under gentle stirring for 1 h at room temperature. Subsequently the reaction mixture was applied onto an equilibrated ion-exchange chromatography resin (Fractogel EMD TMAE 650M) in 20 mM HEPES buffer, 150 mM NaCl, pH 7.4, containing 0.5% sucrose. Then the column was washed with 20 CV equilibration buffer to remove excess reagent and the PEGylated rVWF dimer was eluted with elution buffer (20 mM HEPES, 0.5 M NaCl, 0.5% sucrose, pH 7.4). The eluate was concentrated by ultrafiltration/diafiltration with a membrane consisting of regenerated cellulose (Millipore) and with a molecular weight cut-off of 100 kD using a buffer system consisting of 20 mM HEPES, 150 mM NaCl, 0.5% sucrose, pH 7.4.

Example 41

PEGylation and in vitro Characterization of Low Multimer rVWF

Mature rVWF was purified according to Example 23. The purification procedure included ion-exchange chromatography steps as well as a final gelfiltration step on Superose 6, performed in 20 mM HEPES, 150 mM NaCl, pH 7.4, where the high multimer rVWF (17 multimers) was eluted in the void volume. The VWF multimer analysis was performed according to Ruggeri and Zimmerman (Blood 57: 1140-43, 1981) using a 1.0% agarose gel. A low multimer rVWF preparation (6 multimers) was obtained from a side fraction, eluting at higher retention times. This fraction was stabilized by addition of 0.5% sucrose, pH 7.4. Then the low multimer rVWF was PEGylated using mPEG succinimidyl succinate (PEG-SS). The PEG-SS was added to this solution under gentle stirring (5 mg PEG-SS/mg protein) and the pH value was adjusted to 7.4 by drop wise addition of 0.5 M NaOH. The PEGylation was carried out under gentle stirring for 1 h at room temperature. Subsequently the excess reagent was removed by ultrafiltration/diafiltration with a membrane consisting of regenerated cellulose and with a molecular weight cut-off of 100 kD using a buffer system consisting of 20 mM HEPES, 150 mM NaCl, 0.5% sucrose, pH 7.4. The FVIII binding capacity determined by the ECA assay according to Example 16 slightly decreased from 49% for the starting material to 34% for the PEGylated preparation. The VWF:RCoNWF:Ag ratio of 0.02 measured for the low multimer rVWF was not affected by the PEGylation procedure.

Example 42

Derivatization of VWF with Reversibly Blocked FVIII Binding Epitopes (Blocking with FVIII and Heparin)

A chromatographic column (15 mm×148 mm) was filled with Heparin HyperD (Bio-Sepra) and equilibrated with an equilibration buffer consisting of 20 mM HEPES, 68 mM NaCl, 0.5% sucrose, pH 7.4. Then a solution of mature rVWF (48 IU VWF:Ag/ml) in 20 mM HEPES, 150 mM NaCl, 0.5 sucrose was diluted with H₂O to give a conductivity of 7-8 mS/cm and applied onto this column using a linear flow rate of 1.5 cm/min. Subsequently branched mPEG succinimidyl glutarate (chain length: 20 kD) supplied by NOF corporation (NOF Europe, Grobbendonk. Belgium) was freshly dissolved in 15 ml equilibration buffer to give a final concentration of 5 mg PEG-SG/mg bound protein. Then this reagent solution was pumped onto the column and the PEGylation was carried out for 2 hours under static conditions. Then the column was washed with 10 CV equilibration buffer containing 0.05% lysine. Then the PEGylated rVWF with protected FVIII binding epitope was eluted with a buffer consisting of 20 mM HEPES, 1 M NaCl, 0.5% sucrose, pH 7.4. Finally this solution was concentrated by ultrafiltration/diafiltration against 20 mM HEPES-buffer, pH 7.4 (150 mM NaCl, 0.5% sucrose) using a 100 kD membrane consisting of regenerated cellulose (Millipore). The derivative obtained showed a VWF:RCoNWF:Ag ratio of 0.48, which was identical to the rVWF starting material (ratio 0.47). In contrast to the PEGylation procedure of rVWF with branched PEG-SG 20000 as described in Example 36 the FVIII binding capacity was not affected by this PEGylation procedure with FVIII epitope capping as measure by the

Example 43

Conjugation of VWF with Degradable Peg Via Lysine Residues

A mature rVWF is purified according to Example 23. Then a solution of this rVWF (40 U VWF:Ag/ml) in 20 mM HEPES buffer, 150 mM NaCl, pH 7.4, containing 0.5% sucrose is prepared. Subsequently the PEGylation is carried out by adding mPEG-(carboxymethyl)-3-hydroxy-butanoic acid N-hydroxysuccinimide ester (chain length: 5 kD) to this solution under gentle stirring (5 mg PEG-reagent/mg protein) and the pH value is adjusted to 7.4 by drop wise addition of 0.5 M NaOH. Then the PEGylation reaction is carried out under gentle stirring for 1 h at room temperature. Subsequently the excess reagent is separated from the PEGylated rVWF by ultrafiltration/diafiltration with a membrane consisting of regenerated cellulose and with a molecular weight cut-off of 100 kD using a buffer system consisting of 20 mM HEPES, 150 mM NaCl, 0.5% sucrose, pH 7.4.

The invention claimed is:

1. A proteinaceous molecule comprising, (a) a VWF molecule selected from the group consisting of plasmatic von Willebrand factor (VWF), recombinant VWF, and dimers and multimers thereof; and (b) at least one physiologically acceptable polymer molecule bound to said VWF molecule; said proteinaceous molecule having the capability of binding at least one factor VIII (FVIII) molecule, wherein the in vivo half-life of said proteinaceous molecule is increased as compared to the in vivo half-life of a VWF molecule and the in vivo half-life of said FVIII molecule bound to said proteinaceous molecule is increased as compared to the in vivo half-life of a FVIII molecule not bound to said proteinaceous molecule.

2. The proteinaceous molecule of claim 1 wherein the in vivo half-life of said proteinaceous molecule is increased by at least a factor of about 1.5 as compared to the in vivo half-life of a VWF molecule.

3. The proteinaceous molecule of claim 1 wherein the in vivo half-life of said proteinaceous molecule is increased by at least a factor of about two as compared to the in vivo half-life of a VWF molecule.

4. The proteinaceous molecule of claim 1, wherein said at least one physiologically acceptable polymer molecule is bound to a carbohydrate residue of said VWF.

5. The proteinaceous molecule of claim 1, wherein said at least one physiologically acceptable polymer molecule is bound to a lysine residue of said VWF.

6. The proteinaceous molecule of claim 1, wherein said physiologically acceptable polymer molecule is selected from the group consisting of poly(alkylene glycol), poly(propylene glycol), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(.alpha.-hydroxy acid), poly(vinyl alcohol), polyphosphasphazene, polyoxazoline, and poly(N-acryloylmorpholine).

7. The proteinaceous molecule of claim 1, wherein said physiologically acceptable polymer molecule is polyethylene glycol (PEG) or a derivative thereof.

8. The proteinaceous molecule of claim 1, wherein said physiologically acceptable polymer molecule is polysialic acid (PSA) or a derivative thereof.

9. The proteinaceous molecule of claim 1 wherein said VWF comprised in said proteinaceous molecule retains the biological activity in primary hemostasis of VWF, said biological activity comprising binding to receptors on platelets and on components of extracellular matrix, said components including collagen.

10. The proteinaceous molecule of claim 1 wherein the in vivo half-life of said FVIII molecule, when bound to said proteinaceous molecule, is increased by at least a factor of about 1.5 as compared to the in vivo half-life of a FVIII molecule not bound to said proteinaceous molecule.

11. The proteinaceous molecule of claim 1 wherein the in vivo half-life of said FVIII molecule, when bound to said proteinaceous molecule, is increased by at least a factor of about two as compared to the in vivo half-life of a FVIII molecule not bound to said proteinaceous molecule.

12. The proteinaceous molecule of claim 1 wherein said VWF is a recombinant product.

13. A complex comprising the proteinaceous molecule of claim 1 and at least one FVIII molecule.

14. The complex of claim 13, wherein the FVIII molecule is a recombinant product.

15. A method for prolonging the in vivo half-life of FVIII in the blood of a mammal having a bleeding disorder associated with functional defects of or deficiencies of FVIII, comprising the steps of: (a) administering a first dose of at least one proteinaceous molecule of claim 1 to said mammal; and (b) administering a first dose of at least one FVIII molecule to said mammal.

16. A method for prolonging the in vivo half-life of FVIII and VWF in the blood of a mammal having a bleeding disorder associated with functional defects of at least one of FVIII and VWF, comprising the steps of: (a) administering a first dose of at least one proteinaceous molecule of claim 1 to said mammal; and (b) administering a first dose of at least one FVIII molecule to said mammal.

17. A method for prolonging the in vivo half-life of Factor VIII (FVIII) and vWF in the blood of a mammal having a bleeding disorder associated with functional defects of or deficiencies of at least one of FVIII and VWF, comprising the steps of: (a) providing at least one proteinaceous molecule of claim 1; (b) providing at least one FVIII molecule; and (c) forming a complex between said proteinaceous molecule and said FVIII molecule.

18. A method for prolonging the in vivo half-life of Factor VIII (FVIII) in the blood of a mammal having a bleeding disorder associated with functional defects or disorder associated with function defects of or deficiencies of FVIII, comprising the steps of: (a) providing at least one proteinaceous molecule of claim 1; (b) providing at least one FVIII molecule; and (c) forming a complex between said proteinaceous molecule and said FVIII molecule.

19. The method of claim 17 or 18, wherein the complex of step (c) is administered to said mammal.

20. The method of claim 15 or 16, wherein the at least one FVIII molecule is administered simultaneously with said proteinaceous molecule.

21. The method of claim 15 or 16, wherein the at least one FVIII molecule is administered sequentially before or after the administration of said proteinaceous molecule.

22. A pharmaceutical composition comprising an effective amount of the proteinaceous molecule of claim 1, 2, 3, 6, 10 or 11 and one or more compounds selected from the group consisting of a pharmaceutically acceptable carrier, diluent, salt, buffer, and excipient.

23. A complex comprising, (a) a proteinaceous molecule of claim 1 comprising; (i) a VWF molecule selected from the group consisting of plasmatic von Willebrand factor (VWF), recombinant VWF, and dimers and multimers thereof; and (ii) at least one physiologically acceptable polymer molecule bound to said VWF molecule; and (b) at least one FVIII molecule bound to said proteinaceous molecule; wherein the in vivo half-life of said complex is increased as compared to the in vivo half-life of a FVIII bound to VWF.

24. The complex of claim 23 wherein the in vivo half-life of said complex is increased by a factor of at least about 1.5 as compared to the in vivo half-life of a FVIII bound to VWF.

25. The complex of claim 23 wherein the in vivo half-life of said complex is increased by a factor of at least about two as compared to the in vivo half-life of a FVIII bound to VWF.

26. The proteinaceous molecule of claim 1 comprising a VWF molecule and a PEG moiety covalently bound to at least one carbohydrate residue on said VWF molecule, prepared by a method comprising; a) providing a VWF molecule selected from the group consisting of plasmatic von Willebrand factor (VWF), recombinant VWF, and dimers and multimers thereof; b) oxidizing carbohydrate residues on said VWF molecule; c) contacting said carbohydrate residues with a PEG reagent containing a hydrazide group; and d) allowing said reagent PEG hydrazide to covalently bind to at least one carbohydrate residue on said VWF, thereby forming said proteinaceous molecule, wherein the in vivo half-life of said proteinaceous molecule is increased as compared to the in vivo half-life of a VWF molecule, and wherein said proteinaceous molecule is capable of binding at least one FVIII molecule.

27. The proteinaceous molecule of claim 26 wherein the in vivo half-life of said proteinaceous molecule is increased by a factor of at least about 1.5 as compared to the in vivo half-life of a VWF molecule.

28. The proteinaceous molecule of claim 26 wherein the in vivo half-life of said proteinaceous molecule is increased by a factor of at least about two as compared to the in vivo half-life of a VWF molecule.

29. The proteinaceous molecule of claim 26 wherein the in vivo half-life of a FVIII molecule when bound to said proteinaceous molecule, is increased by at least a factor of about 1.5 as compared to the in vivo half-life of said FVIII molecule not bound to said proteinaceous molecule.

30. The proteinaceous molecule of claim 26 wherein the in vivo half-life of a FVIII molecule when bound to said proteinaceous molecule, is increased by at least a factor of about two as compared to the in vivo half-life of said FVIII molecule not bound to said proteinaceous molecule.

31. The proteinaceous molecule of claim 1 comprising a VWF molecule and a PEG moiety covalently bound to at least one primary amino group by reductive amination on said VWF molecule, prepared by a method comprising; a) providing a VWF molecule selected from the group consisting of plasmatic von Willebrand factor (VWF), recombinant VWF, and dimers and multimers thereof; b) contacting lysine residues on said VWF molecule with a PEG reagent containing an aldehyde group to form a Schiff base in solution; c) contacting said solution with a reducing agent to form a secondary amide bond; and d) allowing said PEG reagent to covalently bind to said VWF molecule, thereby forming said proteinaceous molecule, wherein the in vivo half-life of said proteinaceous molecule is increased as compared to the in vivo half-life of a VWF molecule, and wherein said proteinaceous molecule is capable of binding at least one factor VIII (FVIII) molecule.

32. The proteinaceous molecule of claim 31 wherein the in vivo half-life of said proteinaceous molecule is increased by a factor of at least 1.5 as compared to the in vivo half-life of a VWF molecule.

33. The proteinaceous molecule of claim 31 wherein the in vivo half-life of said proteinaceous molecule is increased by a factor of at least two as compared to the in vivo half-life of a VWF molecule.

34. The proteinaceous molecule of claim 31 wherein the in vivo half-life of a FVIII molecule when bound to said proteinaceous molecule, is increased by at least a factor of 1.5 as compared to the in vivo half-life of said FVIII molecule not bound to said proteinaceous molecule.

35. The proteinaceous molecule of claim 31 wherein the in vivo half-life of a FVIII molecule when bound to said proteinaceous molecule, is increased by at least a factor of two as compared to the in vivo half-life of said FVIII molecule not bound to said proteinaceous molecule.

36. The proteinaceous molecule of claim 1 comprising a VWF molecule and a PEG moiety covalently bound to at least one free or generated sulfhydryl group on said VWF molecule, prepared by a method comprising; a) providing a VWF molecule selected from the group consisting of plasmatic von Willebrand factor (VWF), recombinant VWF, and dimers and multimers thereof; b) contacting said sulfhydryl group on said VWF molecule with a PEG reagent containing a maleimide group; and c) allowing said PEG reagent to covalently bind to at least one sulfhydryl group on said VWF, thereby forming said proteinaceous molecule, wherein the in vivo half-life of said proteinaceous molecule is increased as compared to the in vivo half-life of a VWF molecule, and wherein said proteinaceous molecule is capable of binding at least one factor VIII (FVIII) molecule.

37. The proteinaceous molecule of claim 36 wherein the in vivo half-life of said proteinaceous molecule is increased by a factor of at least 1.5 as compared to the in vivo half-life of a VWF molecule.

38. The proteinaceous molecule of claim 36 wherein the in vivo half-life of said proteinaceous molecule is increased by a factor of at least two as compared to the in vivo half-life of a VWF molecule.

39. The proteinaceous molecule of claim 36 wherein the in vivo half-life of a FVIII molecule when bound to said proteinaceous molecule, is increased by at least a factor of 1.5 as compared to the in vivo half-life of said FVIII molecule not bound to said proteinaceous molecule.

40. The proteinaceous molecule of claim 36 wherein the in vivo half-life of a FVIII molecule when bound to said proteinaceous molecule, is increased by at least a factor of two as compared to the in vivo half-life of said FVIII molecule not bound to said proteinaceous molecule.

41. The proteinaceous molecule of claim 1 comprising a VWF molecule and a PEG moiety covalently bound to at least one carboxyl group on said VWF molecule, prepared by a method comprising; a) providing a VWF molecule selected from the group consisting of plasmatic von Willebrand factor (VWF), recombinant VWF, and dimers and multimers thereof; b) contacting carboxyl groups on said VWF molecule with a PEG reagent containing an amino group and a water soluble carbodiimide to form an amide bond; and c) allowing said PEG moiety to covalently bind to said VWF, thereby forming said proteinaceous molecule, wherein the in vivo half-life of said proteinaceous molecule is increased as compared to the in vivo half-life of a VWF molecule, and wherein said proteinaceous molecule is capable of binding at least one FVIII molecule.

42. The proteinaceous molecule of claim 41 wherein the in vivo half-life of said proteinaceous molecule is increased by a factor of at least 1.5 as compared to the in vivo half-life of a VWF molecule.

43. The proteinaceous molecule of claim 41 wherein the in vivo half-life of said proteinaceous molecule is increased by a factor of at least two as compared to the in vivo half-life of a VWF molecule.

44. The proteinaceous molecule of claim 41 wherein the in vivo half-life of a FVIII molecule when bound to said proteinaceous molecule, is increased by at least a factor of 1.5 as compared to the in vivo half-life of said FVIII molecule not bound to said proteinaceous molecule.

45. The proteinaceous molecule of claim 41 wherein the in vivo half-life of a FVIII molecule when bound to said proteinaceous molecule, is increased by at least a factor of two as compared to the in vivo half-life of said FVIII molecule not bound to said proteinaceous molecule.

46. The proteinaceous molecule of claim 1 comprising a VWF molecule and a PEG moiety covalently bound to said VWF molecule, said PEG moiety not being bound to the FVIII binding site of said VWF molecule, prepared by a method comprising; a) providing a VWF molecule selected from the group consisting of plasmatic von Willebrand factor (VWF), recombinant VWF, and dimers and multimers thereof; b) contacting the FVIII binding site on said VWF molecule with a Factor VIII-binding-site-protecting agent, thereby forming a VWF molecule with a protected FVIII binding site; c) contacting a reactive site on said VWF molecule of step (b) with a PEG reagent; d) allowing said PEG reagent to covalently bind to said VWF molecule; and e) separating said FVIII-binding-site-protecting agent from said. VWF molecule, thereby forming said proteinaceous molecule wherein the in vivo half-life of said proteinaceous molecule is increased as compared to the in vivo half-life of a VWF molecule, and wherein said proteinaceous molecule is capable of binding at least one factor VIII (FVIII) molecule.

47. The proteinaceous molecule of claim 46 wherein the in vivo half-life of said proteinaceous molecule is increased by a factor of at least 1.5 as compared to the in vivo half-life of a VWF molecule.

48. The proteinaceous molecule of claim 46 wherein the in vivo half-life of said proteinaceous molecule is increased by a factor of at least two as compared to the in vivo half-life of a VWF molecule.

49. The proteinaceous molecule of claim 46 wherein the in vivo half-life of a FVIII molecule when bound to said proteinaceous molecule, is increased by at least a factor of 1.5 as compared to the in vivo half-life of said FVIII molecule not bound to said proteinaceous molecule.

50. The proteinaceous molecule of claim 46 wherein the in vivo half-life of a FVIII molecule when bound to said proteinaceous molecule, is increased by at least a factor of two as compared to the in vivo half-life of said FVIII molecule not bound to said proteinaceous molecule.

51. The proteinaceous molecule of claim 1 comprising a VWF molecule and a sialic acid (PSA) moiety covalently bound to at least one lysine residue on said VWF molecule, prepared according to a method comprising; a) providing a VWF molecule selected from the group consisting of plasmatic von Willebrand factor (VWF), recombinant VWF, and dimers and multimers thereof; b) contacting a PSA with a PEG reagent containing an aldehyde to form a Schiff base in solution; c) contacting said solution with a reducing agent to form a secondary amide bond; and d) allowing said PSA to covalently bind to at least one lysine residue on said VWF, thereby forming said proteinaceous molecule, wherein the in vivo half-life of said proteinaceous molecule is increased as compared to the in vivo half-life of a VWF molecule, and wherein said proteinaceous molecule is capable of binding at least one FVIII molecule.

52. The proteinaceous molecule of claim 51 wherein the in vivo half-life of said proteinaceous molecule is increased by a factor of at least 1.5 as compared to the in vivo half-life of a VWF molecule.

53. The proteinaceous molecule of claim 51 wherein the in vivo half-life of said proteinaceous molecule is increased by a factor of at least two as compared to the in vivo half-life of a VWF molecule.

54. The proteinaceous molecule of claim 51 wherein the in vivo half-life of a FVIII molecule when bound to said proteinaceous molecule, is increased by at least a factor of 1.5 as compared to the in vivo half-life of said FVIII molecule not bound to said proteinaceous molecule.

55. The proteinaceous molecule of claim 51 wherein the in vivo half-life of a FVIII molecule when bound to said proteinaceous molecule, is increased by at least a factor of two as compared to the in vivo half-life of said FVIII molecule not bound to said proteinaceous molecule.

56. The proteinaceous molecule of claim 1 comprising a VWF molecule and a polysialic acid (PSA) moiety covalently cross-linked to said VWF molecule, prepared by a method comprising; a) providing a VWF molecule selected from the group consisting of plasmatic von Willebrand factor (VWF), recombinant VWF, and dimers and multimers thereof; b) contacting said VWF molecule with a solution containing PSA and glutaraldehyde; and c) allowing said PSA to be covalently cross-linked to said VWF, thereby forming said proteinaceous molecule wherein the in vivo half-life of said proteinaceous molecule is increased as compared to the in vivo half-life of a VWF molecule, and wherein said proteinaceous molecule is capable of binding at least one FVIII molecule.

57. The proteinaceous molecule of claim 56 wherein the in vivo half-life of said proteinaceous molecule is increased by a factor of at least 1.5 as compared to the in vivo half-life of a VWF molecule.

58. The proteinaceous molecule of claim 56 wherein the in vivo half-life of said proteinaceous molecule is increased by a factor of at least two as compared to the in vivo half-life of a VWF molecule.

59. The proteinaceous molecule of claim 56 wherein the in vivo half-life of a FVIII molecule when bound to said proteinaceous molecule, is increased by at least a factor of 1.5 as compared to the in vivo half-life of said FVIII molecule not bound to said proteinaceous molecule.

60. The proteinaceous molecule of claim 56 wherein the in vivo half-life of a FVIII molecule when bound to said proteinaceous molecule, is increased by at least a factor of two as compared to the in vivo half-life of said FVIII molecule not bound to said proteinaceous molecule.

61. The proteinaceous molecule of claim 1 comprising a VWF molecule and a hyaluronic acid (HA) moiety covalently bound to at least one lysine residue on said VWF molecule, prepared by a method comprising; a) providing a VWF molecule selected from the group consisting of plasmatic von Willebrand factor (VWF), recombinant VWF, and dimers and multimers thereof; b) contacting a solution of HA with an oxidizing agent to form activated HA; c) contacting said VWF molecule with said activated HA, thereby forming said proteinaceous molecule, wherein the in vivo half-life of said proteinaceous molecule is increased as compared to the in vivo half-life of a VWF molecule, and wherein said proteinaceous molecule is capable of binding at least one factor FVIII molecule.

62. The proteinaceous molecule of claim 61 wherein the in vivo half-life of said proteinaceous molecule is increased by a factor of at least 1.5 as compared to the in vivo half-life of a VWF molecule.

63. The proteinaceous molecule of claim 61 wherein the in vivo half-life of said proteinaceous molecule is increased by a factor of at least two as compared to the in vivo half-life of a VWF molecule.

64. The proteinaceous molecule of claim 61 wherein the in vivo half-life of a FVIII molecule when bound to said proteinaceous molecule, is increased by at least a factor of 1.5 as compared to the in vivo half-life of said FVIII molecule not bound to said proteinaceous molecule.

65. The proteinaceous molecule of claim 61 wherein the in vivo half-life of a FVIII molecule when bound to said proteinaceous molecule, is increased by at least a factor of two as compared to the in vivo half-life of said FVIII molecule not bound to said proteinaceous molecule.

66. The proteinaceous molecule of claim 1 comprising a VWF molecule and a PEG moiety covalently bound to at least one carbohydrate group on said VWF molecule, prepared by a method comprising; a) providing a VWF molecule selected from the group consisting of plasmatic von Willebrand factor (VWF), recombinant VWF, and dimers and multimers thereof; b) contacting a carbohydrate group on said VWF molecule with an oxidizing enzyme to form an oxidized carbohydrate moiety on said VWF; c) contacting said oxidized carbohydrate moiety on said VWF with a PEG reagent containing a hydrazide group; and d) allowing said PEG moiety to covalently bind to said VWF, thereby forming said proteinaceous molecule, wherein the in vivo half-life of said proteinaceous molecule is increased as compared to the in vivo half-life of a VWF molecule, and wherein said proteinaceous molecule is capable of binding at least one FVIII molecule.

67. The proteinaceous molecule of claim 66 wherein the in vivo half-life of said proteinaceous molecule is increased by a factor of at least 1.5 as compared to the in vivo half-life of a VWF molecule.

68. The proteinaceous molecule of claim 66 wherein the in vivo half-life of said proteinaceous molecule is increased by a factor of at least two as compared to the in vivo half-life of a VWF molecule.

69. The proteinaceous molecule of claim 66 wherein the in vivo half-life of a FVIII molecule when bound to said proteinaceous molecule, is increased by at least a factor of 1.5 as compared to the in vivo half-life of said FVIII molecule not bound to said proteinaceous molecule.

70. The proteinaceous molecule of claim 66 wherein the in vivo half-life of a FVIII molecule when bound to said proteinaceous molecule, is increased by at least a factor of two as compared to the in vivo half-life of said FVIII molecule not bound to said proteinaceous molecule.

71. The proteinaceous molecule of claim 1 comprising a VWF molecule and a PEG moiety covalently bound to said VWF molecule, prepared by a method comprising; a) providing a VWF molecule selected from the group consisting of plasmatic von Willebrand factor (VWF), recombinant VWF, and dimers and multimers thereof; b) contacting said VWF molecule with a PEG reagent to form a solution; c) placing said solution into a perfusion chamber whereby shear stress is created on said VWF molecule by use of a peristaltic pump; and c) allowing said PEG reagent to covalently bind to said VWF, thereby forming said proteinaceous molecule, wherein the in vivo half-life of said proteinaceous molecule is increased as compared to the in vivo half-life of a VWF molecule, and wherein said proteinaceous molecule is capable of binding at least one FVIII molecule.

72. The proteinaceous molecule of claim 71 wherein the in vivo half-life of said proteinaceous molecule is increased by a factor of at least 1.5 as compared to the in vivo half-life of a VWF molecule.

73. The proteinaceous molecule of claim 71 wherein the in vivo half-life of said proteinaceous molecule is increased by a factor of at least two as compared to the in vivo half-life of a VWF molecule.

74. The proteinaceous molecule of claim 71 wherein the in vivo half-life of a FVIII molecule when bound to said proteinaceous molecule, is increased by at least a factor of 1.5 as compared to the in vivo half-life of said FVIII molecule not bound to said proteinaceous molecule.

75. The proteinaceous molecule of claim 71 wherein the in vivo half-life of a FVIII molecule when bound to said proteinaceous molecule, is increased by at least a factor of two as compared to the in vivo half-life of said FVIII molecule not bound to said proteinaceous molecule.

76. The proteinaceous molecule of claim 1, wherein said at least one physiologically acceptable polymer molecule is bound to a carbohydrate residue of said VWF.

77. The proteinaceous molecule of claim 1, wherein said at least one physiologically acceptable polymer molecule is bound to a lysine residue of said VWF.

78. The proteinaceous molecule of claim 1, wherein said physiologically acceptable polymer molecule is selected from the group consisting of poly(alkylene glycol), poly(propylene glycol), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly (.alpha.-hydroxy acid), poly(vinyl alcohol), polyphosphasphazene, polyoxazoline, and poly(N-acryloylmorpholine).

79. The proteinaceous molecule of claim 1, wherein said physiologically acceptable polymer molecule is polyethylene glycol (PEG) or a derivative thereof.

80. The proteinaceous molecule of claim 1, wherein said physiologically acceptable polymer molecule is polysialic acid (PSA) or a derivative thereof.

81. The proteinaceous molecule of claim 1, wherein said VWF comprised in said proteinaceous molecule retains the biological activity in primary hemostasis of VWF, said biological activity comprising binding to receptors on platelets and on components of extracellular matrix, said components including collagen.

82. The proteinaceous molecule of claim 1, wherein said physiologically acceptable polymer molecule is selected from the group consisting of poly(alkylene glycol), poly(propylene glycol), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly (.alpha.-hydroxy acid), poly(vinyl alcohol), polyphosphasphazene, polyoxazoline, and poly(N-acryloylmorpholine).

83. The complex of claim 23, wherein said physiologically acceptable polymer molecule is polyethylene glycol (PEG) or a derivative thereof.

84. The complex of claim 24, wherein said physiologically acceptable polymer molecule is polyethylene glycol (PEG) or a derivative thereof.

85. The complex of claim 24, wherein said physiologically acceptable polymer molecule is polysialic acid (PSA) or a derivative thereof.

* * * * *

UNITED STATES PATENT AND TRADEMARK OFFICE
CERTIFICATE OF CORRECTION

| | | |
|---|---|---|
| PATENT NO. | : 7,884,075 B2 | |
| APPLICATION NO. | : 11/317582 | |
| DATED | : February 8, 2011 | |
| INVENTOR(S) | : Friedrich Scheiflinger et al. | |

It is certified that error appears in the above-identified patent and that said Letters Patent is hereby corrected as shown below:

On the Title Page:

Item (54), "POLYMER-FACTOR VIII-VON WILLEBRAND FACTOR-CONJUGATES" should be -- POLYMER-VON WILLEBRAND FACTOR-CONJUGATES --.

At Column 1, lines 1-2, "POLYMER-FACTOR VIII-VON WILLEBRAND FACTOR-CONJUGATES" should be -- POLYMER-VON WILLEBRAND FACTOR-CONJUGATES --.

Signed and Sealed this
Sixth Day of December, 2011

David J. Kappos
*Director of the United States Patent and Trademark Office*